US012765888B2

(12) United States Patent
Wolfe et al.

(10) Patent No.: US 12,765,888 B2
(45) Date of Patent: Oct. 20, 2026

(54) METAPHYSEAL REFERENCING TECHNIQUE AND INSTRUMENT

(71) Applicant: HOWMEDICA OSTEONICS CORP., Mahwah, NJ (US)

(72) Inventors: Alexander Paul Wolfe, Fort Wayne, IN (US); David R. Stump, Columbia City, IN (US); Kevin P. Knox, Fort Wayne, IN (US); Anne Marie Schlamb, Leesburg, IN (US); George S. Athwal, London (CA); R. Sean Churchill, Mequon, WI (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 623 days.

(21) Appl. No.: 17/793,447

(22) PCT Filed: Mar. 22, 2021

(86) PCT No.: PCT/US2021/023439

§ 371 (c)(1),
(2) Date: Jul. 18, 2022

(87) PCT Pub. No.: WO2021/194949

PCT Pub. Date: Sep. 30, 2021

(65) Prior Publication Data

US 2023/0038980 A1 Feb. 9, 2023

Related U.S. Application Data

(60) Provisional application No. 62/994,699, filed on Mar. 25, 2020.

(51) Int. Cl.

*A61B 17/17* (2006.01)
*A61B 17/00* (2006.01)
*A61B 90/00* (2016.01)

(52) U.S. Cl.

CPC .......... *A61B 17/17* (2013.01); *A61B 17/1717* (2013.01); *A61B 17/1778* (2016.11);
(Continued)

(58) Field of Classification Search

CPC ............ A61B 17/1717; A61B 17/1778; A61B 2090/036; A61B 2090/033
See application file for complete search history.

(56) References Cited

U.S. PATENT DOCUMENTS 4,305,394 A * 12/1981 Bertuch, Jr. .......... A61F 2/4609
606/104
4,433,686 A * 2/1984 Charnley ............. A61F 2/4684
606/86 R
(Continued)

FOREIGN PATENT DOCUMENTS

AU 2004316388 B2 1/2011
CA 2209498 A1 8/1996
(Continued)

OTHER PUBLICATIONS

Extended European Search Report issued in connection with European Patent Application No. 21775719.4, Feb. 20, 2024, 15 pages.
(Continued)

*Primary Examiner* — David W Bates
(74) *Attorney, Agent, or Firm* — DUANE MORRIS LLP

(57) ABSTRACT

Guides for guiding a tool into a medullary canal of a bone. The guides can include a base and a guide feature. The base can include a first surface configured to contact the bone and a second surface opposite the first surface. The guide feature can be disposed to guide the tool along a central portion of the medullary canal.

28 Claims, 27 Drawing Sheets

(52) U.S. Cl.
CPC . *A61B 2017/0046* (2013.01); *A61B 2090/033* (2016.02); *A61B 2090/067* (2016.02)

(56) References Cited

U.S. PATENT DOCUMENTS

RE31,865 E * 4/1985 Roux ........................ A61F 2/32 623/22.14
4,528,980 A * 7/1985 Kenna ................ A61B 17/1746 606/80
4,662,891 A * 5/1987 Noiles ................... A61F 2/4609 623/22.25
4,904,265 A * 2/1990 MacCollum .............. A61F 2/34 623/22.28
5,030,219 A * 7/1991 Matsen, III ........ A61B 17/1778 606/86 R
5,284,483 A * 2/1994 Johnson ................ A61F 2/4609 606/86 R
5,534,032 A * 7/1996 Hodorek ............. A61F 2/30721 411/537
5,609,642 A * 3/1997 Johnson .................. A61F 2/461 606/88
5,630,819 A * 5/1997 Ashby ................... A61F 2/4601 606/86 R
5,634,927 A * 6/1997 Houston ............ A61B 17/1764 606/88
5,693,055 A * 12/1997 Zahiri ................ A61B 17/8061 606/65
5,702,477 A * 12/1997 Capello ............... A61F 2/30724 623/22.21
5,769,856 A * 6/1998 Dong ................. A61B 17/1778 606/80
5,779,710 A * 7/1998 Matsen, III ............ A61B 17/15 606/102
5,976,147 A * 11/1999 LaSalle .............. A61B 17/1764 606/88
6,117,138 A * 9/2000 Burrows ............... A61F 2/4684 606/86 R
6,143,012 A * 11/2000 Gausepohl ......... A61B 17/1717 606/67
6,152,930 A * 11/2000 Mastrorio ............. A61F 2/4609 606/91
6,267,785 B1 * 7/2001 Masini ................ A61F 2/30724 623/23.22
6,283,999 B1 9/2001 Rockwood, Jr.
6,334,874 B1 1/2002 Tornier et al.
6,398,812 B1 6/2002 Masini
7,353,153 B2 4/2008 Ascenzi et al.
7,435,263 B2 10/2008 Barnett et al.
7,527,631 B2 * 5/2009 Maroney ................ A61B 90/06 606/102
7,699,853 B2 4/2010 Durand-Allen et al.
8,062,299 B2 * 11/2011 McGahan ............ A61B 17/025 606/82
8,078,440 B2 12/2011 Otto et al.
8,277,450 B2 10/2012 Dees, Jr. et al.
8,545,506 B2 * 10/2013 Long ......................... A61F 2/40 606/86 R
8,562,616 B2 * 10/2013 May .......................... A61F 2/38 623/20.14
8,574,235 B2 11/2013 Stone
8,768,674 B2 7/2014 Darwish et al.
9,271,744 B2 * 3/2016 Meridew ............ A61B 17/1746
9,408,616 B2 * 8/2016 Kehres ................... A61B 17/15
9,498,233 B2 * 11/2016 Eash ..................... A61F 2/4609
9,662,219 B2 5/2017 Bonin, Jr. et al.
9,763,682 B2 * 9/2017 Bettenga ............ A61B 17/1666
10,987,175 B2 4/2021 Britton et al.
11,229,524 B2 1/2022 Sperling
11,234,721 B2 * 2/2022 Gargac ............... A61B 17/1778
11,266,503 B2 3/2022 Coulange et al.
11,559,405 B2 1/2023 Yadav et al.
11,703,096 B2 7/2023 Denhard et al.
11,980,376 B2 * 5/2024 Luttrell ................ A61B 17/151
12,090,057 B2 9/2024 Courtade-Jouanicq et al.
12,251,118 B2 * 3/2025 Gargac .................. A61F 2/4081
2003/0014119 A1 1/2003 Capon et al.
2003/0060889 A1 3/2003 Tarabishy
2003/0078669 A1 * 4/2003 Martin .................. A61F 2/3607 623/20.32
2004/0162619 A1 * 8/2004 Blaylock ............. A61F 2/30734 606/88
2005/0101961 A1 * 5/2005 Huebner ............ A61B 17/8605 606/305
2005/0107797 A1 5/2005 Romeo
2005/0177241 A1 8/2005 Angibaud et al.
2006/0009854 A1 1/2006 Justin et al.
2006/0015188 A1 * 1/2006 Grimes ................. A61F 2/3601 623/23.22
2007/0244565 A1 10/2007 Stchur
2008/0004517 A1 1/2008 Bhandarkar et al.
2008/0015599 A1 * 1/2008 D'Alessio ............ A61B 17/155 606/79
2008/0183297 A1 * 7/2008 Boileau .............. A61B 17/1637 623/16.11
2009/0265010 A1 10/2009 Angibaud et al.
2009/0270867 A1 10/2009 Poncet
2009/0318927 A1 * 12/2009 Martin ............... A61B 17/1764 606/96
2010/0049260 A1 2/2010 Long et al.
2010/0217400 A1 8/2010 Nortman et al.
2010/0234850 A1 9/2010 Dees, Jr. et al.
2011/0224673 A1 9/2011 Smith
2011/0224799 A1 9/2011 Stone
2011/0282462 A1 11/2011 Wunderle et al.
2012/0035733 A1 2/2012 Porter et al.
2012/0123423 A1 * 5/2012 Fryman ................ A61B 17/175 606/89
2012/0296339 A1 11/2012 Iannotti et al.
2013/0006253 A1 * 1/2013 Waite, II ............ A61B 17/1675 606/88
2013/0041376 A1 * 2/2013 Neal .................. A61B 17/1764 606/88
2013/0204259 A1 * 8/2013 Zajac ................. A61B 17/1764 606/88
2013/0261622 A1 10/2013 Bonjour et al.
2013/0304220 A1 * 11/2013 Bonitati .............. A61F 2/30734 623/20.15
2013/0325136 A1 * 12/2013 Thomas ............. A61B 17/1735 623/20.32
2013/0325430 A1 12/2013 Darwish et al.
2014/0012266 A1 1/2014 Bonin et al.
2014/0074174 A1 * 3/2014 Schacherer ........ A61B 17/8061 606/86 R
2014/0276850 A1 9/2014 Chaney et al.
2014/0276857 A1 * 9/2014 Major ................... A61F 2/3868 606/88
2014/0330390 A1 11/2014 Liu et al.
2014/0363481 A1 12/2014 Pasini et al.
2015/0190151 A1 * 7/2015 Budhabhatti ...... A61B 17/1666 606/96
2015/0190237 A1 7/2015 Bonin, Jr. et al.
2015/0250601 A1 * 9/2015 Humphrey ............ A61F 2/4014 606/80
2015/0313727 A1 * 11/2015 Waite, II ............ A61B 17/1764 623/20.32
2016/0158021 A1 6/2016 Goldberg et al.
2016/0270797 A1 * 9/2016 Sweitzer ............ A61B 17/1637
2016/0287266 A1 * 10/2016 Sikora ................... A61F 2/4081
2016/0287395 A1 10/2016 Khalili et al.
2017/0000503 A1 * 1/2017 Keefer ............... A61B 17/1615
2017/0007275 A1 * 1/2017 Park ....................... A61B 34/10
2017/0049573 A1 2/2017 Hodorek et al.
2017/0079800 A1 3/2017 Messieh
2017/0209278 A1 * 7/2017 Roach ..................... A61F 2/389
2017/0239058 A1 8/2017 Goldberg
2017/0304063 A1 * 10/2017 Hatzidakis ............ A61F 2/4003
2017/0333215 A1 * 11/2017 Wolfson ................ A61F 2/4684
2018/0132687 A1 * 5/2018 Reeves .................... A47L 9/106
2018/0206854 A1 * 7/2018 Dees .................... A61B 17/164
2018/0250138 A1 9/2018 Alidousti et al.
2018/0318093 A1 11/2018 Kirwan

(56) References Cited

U.S. PATENT DOCUMENTS

| | | | | |
|---|---|---|---|---|
| 2019/0015119 | A1* | 1/2019 | Athwal | A61F 2/4612 |
| 2019/0046326 | A1* | 2/2019 | Ball | A61F 2/40 |
| 2019/0105169 | A1 | 4/2019 | Sperling | |
| 2019/0167356 | A1 | 6/2019 | Britton et al. | |
| 2019/0231544 | A1 | 8/2019 | Boileau et al. | |
| 2019/0240030 | A1 | 8/2019 | Coulange et al. | |
| 2019/0274697 | A1* | 9/2019 | Santangelo | A61B 17/1764 |
| 2019/0298543 | A1 | 10/2019 | Hashida et al. | |
| 2020/0383792 | A1* | 12/2020 | Cardon | A61F 2/4612 |
| 2021/0137539 | A1* | 5/2021 | Bahk | A61F 2/30767 |
| 2021/0244546 | A1 | 8/2021 | Yadav et al. | |
| 2021/0338456 | A1* | 11/2021 | Wolfe | A61B 17/1778 |
| 2021/0393414 | A1* | 12/2021 | Robicheaux | A61F 2/40 |
| 2022/0142784 | A1 | 5/2022 | Coulange et al. | |
| 2023/0090775 | A1 | 3/2023 | Yadav et al. | |
| 2023/0101690 | A1 | 3/2023 | Harder et al. | |
| 2023/0404603 | A1* | 12/2023 | Yoko | A61B 17/1764 |
| 2024/0277481 | A1 | 8/2024 | Courtade-Jouanicq et al. | |
| 2024/0341966 | A1 | 10/2024 | Yadav et al. | |

FOREIGN PATENT DOCUMENTS

| | | | | |
|---|---|---|---|---|
| CN | 105263446 A | | 1/2016 | |
| DE | 19532898 A1 | | 3/1997 | |
| EP | 1269941 A1 | | 1/2003 | |
| EP | 1048274 B1 | | 9/2012 | |
| EP | 2769700 A1 | | 8/2014 | |
| EP | 2668928 B1 | | 3/2015 | |
| EP | 2623045 B1 | | 9/2015 | |
| EP | 3335675 A1 | * | 6/2018 | A61F 2/4059 |
| FR | 2965712 A1 | | 4/2012 | |
| JP | 2013521889 A | | 6/2013 | |
| TW | I606813 B | | 12/2017 | |
| WO | 2014035991 A1 | | 3/2014 | |
| WO | 2018175897 A1 | | 9/2018 | |
| WO | 2020072466 A1 | | 4/2020 | |

OTHER PUBLICATIONS

Non-Final Office Action issued in connection with U.S. Appl. No. 16/967,374, filed Jul. 26, 2023, 7 pages.

Restriction Requirement issued in connection with U.S. Appl. No. 17/276,925, filed Dec. 13, 2023, 9 pages.

Partial European Search Report issued in connection with European Patent Application No. 21775719.4, Dec. 7, 2023, 13 pages.

Non-Final Office Action issued in connection with U.S. Appl. No. 17/648,963, Feb. 6, 2025, 22 pages.

Non-Final Office Action issued in connection with U.S. Appl. No. 17/276,925, filed Feb. 22, 2024, 14 pages.

First Office Action issued in connection with Chinese Patent Application No. 201910110195.8, Feb. 21, 2024, 12 pages.

First Office Action issued in connection with Canadian Patent Application No. 3,089,708, Jun. 7, 2024, 9 pages.

Humphrey et al., A Method to Facilitate Improved Positioning of a Reverse Prosthesis Stem During Arthroplasty Surgery: The Metaphyseal-centering Technique, Techniques in Shoulder & Elbow Surgery, Jun. 2018, vol. 19, No. 2, pp. 67-74.

Arthrex Releases Univers Revers™ Shoulder Arthroplasty System in the United States—First Surgery Successfully Performed in Chillicothe, OH, 2013, 2 pages.

International Search Report and Written Opinion dated Mar. 22, 2021 in connection with International Patent Appln. No. PCT/US2021/023439.

Final Rejection issued in connection with U.S. Appl. No. 17/276,925, filed Aug. 5, 2024, 22 pages.

Non-Final Office Action issued in U.S. Appl. No. 18/644,609, filed Aug. 11, 2025, 7 pages.

* cited by examiner

METAPHYSEAL REFERENCING TECHNIQUE AND INSTRUMENT

CROSS-REFERENCE TO RELATED APPLICATIONS

This application is a National Stage Application, filed under 35 U.S.C. 371, of International Patent Application No. PCT/US2021/023439, filed on Mar. 22, 2021, which claims priority to U.S. Provisional Patent Application No. 62/994,699, filed on Mar. 25, 2020, the entire contents of which are incorporated herein by reference.

BACKGROUND

Field

This application is directed to guides for assisting in the preparation of end portions of long bones as part of a joint replacement or repair procedures, particularly for preparing a proximal (or superior) portion of a humerus for implanting a humeral component of an artificial joint.

Description of the Related Art

Arthroplasty is the standard of care for the treatment of shoulder joint arthritis. A typical humeral head replacement is implanted following exposure of the humeral head, resection of the head and various procedures to create space in the humerus for sub-surface stems or anchors to which an artificial head can be coupled. The humeral head replacement might articulate with the native bone or an opposing glenoid resurfacing device, which may be manufactured from ultra-high-molecular-weight polyethylene (UHMWPE) or any other acceptable material.

For more severe cases of shoulder arthritis, the standard treatment is a reverse reconstruction, which includes reversing the kinematics of the shoulder joint. This is performed by securing a semi-spherical device to the glenoid, referred to as a glenoid sphere, and implanting a humeral stem and an articular component coupled to the stem that is capable of receiving the glenoid sphere. In a reverse reconstruction, the humeral stem can attach to a modular tray or include an integrated tray. The tray is configured to receive the articular component.

Preparing the humerus involves resecting the humeral head. Following resection, an awl may be used to create a space that is distal from the resection plane in which the stem or other anchor can be disposed, while a reamer is used to prepare the metaphysis. Historically, reaming is done independently from stem body preparation. However, because there is no link between stem and tray placement, there is the potential for implant misalignment.

SUMMARY

In a diaphyseal referencing technique, a space is first formed in the humerus in the shape of the stem and the metaphyseal or bowl cavity is reamed second. However, due to anatomical offset between the axis of the canal and the center of the humeral head, the bowl or tray may break through a proximal portion of the cortical bone P, which compromises proximal fixation (see FIGS. 1A-1B). In contrast, in a metaphyseal reference technique, the bowl or tray is centered within a resection surface at the proximal end of the humerus and the stem canal is prepared second. However, misalignment between the tray and the stem could lead to distal cortical bone impingement D or distal bone voids V between the canal and the implant, which may compromise stem fixation (see FIGS. 2A-2B).

To solve these issues, the present disclosure is directed toward instruments for evaluating the metaphyseal and diaphyseal axes and techniques for properly implanting a stem and/or tray within a long bone. The instruments include guides that link the position of an implant stem axis to the position of a proximal bowl or tray. For example, the guides can be shaped and/or sized to represent a proximal face and/or a stem inclination angle of different final implant stems. These guides allow the surgeon to evaluate the approximate stem axis position relative to the humeral canal before committing to the bowl placement in the metaphysis. Using these guides, the surgeon can select the appropriate implant and prepare the bone accordingly. This technique transfers the shape of the implant to the bone and ensures proper alignment of the prepared geometry in the bone and the implant geometry. These features also allow the surgeon to visualize the resection angle relative to the humeral canal to help avoid *varus* or valgus implant alignment.

The instrumentation can include a system for sizing the resected surface to provide metaphyseal referencing and to properly guide a tool into a central portion of the canal in the diaphysis. The system can include a sizing feature to approximate the size of the metaphysis. The system can also include a base configured to contact the metaphysis and a guide feature configured to guide a tool along a central portion of the canal in the diaphysis. The sizing feature can be a separate disk component or integral with the base.

The instrumentation can include a guide having a base configured to provide metaphyseal referencing. The base can include a first surface configured to contact the metaphysis (pre- or post-reaming) and a second surface opposite the first surface. The guide can include a guide feature having a central axis disposed to guide a tool, for example an awl or a sounder, into a diaphysis of the bone along a central portion of a canal in the diaphysis. The guide feature can extend into and/or outward of the base.

The guide can form part of a kit including multiple guides. Each guide can be configured to position the tool at a different angle relative to the face of the resection surface and/or the metaphyseal axis. A sizing feature can be included in the kit as a separate disk or integrated into the base of one or more of the humeral guides. The sizing feature can help approximate a size of the metaphysis.

Preparing the long bone can include sizing a proximal portion of the bone to properly center and seat the tray within the metaphysis. A central guide pin may be positioned in the bone to center other instruments. Based on the appropriate sizing, a suitable guide may be selected. After sizing, the metaphysis is prepared using a reamer, and the selected guide can guide a tool down a central portion of the canal. The reaming step can take place prior to beginning canal preparation or after canal preparation begins.

In some implementations, the instrumentation can include a guide having a base and a guide feature. The base can include a first surface configured to contact the bone and a second surface opposite the first surface. The guide feature may include a lumen configured to guide a tool along a central portion of the medullary canal.

In some configurations, the guide may include one or more passageways, e.g., a pair of passageways, disposed about a periphery of the base. Each of the one or more passageways may be configured to receive an osteotome. The one or more passageways may take the form of uncaptured cutouts or captured slots. The captured slots may be defined in a slot member extending from second surface of the base to provide support for the osteotome. The slot member may be integral with or separate from the base.

In some configurations, the guide may include a handle attachment feature extending from a central region of the second surface. The handle attachment feature includes an interface, for example a threaded interface, configured to releasably engage a handle.

In some configurations, the guide may include a cutting feature, e.g., teeth or blades, along at least a portion of a periphery of the base, for example a superior region of the base. The cutting feature may be disposed between the first surface and the second surface of the base. The guide may include a groove on the first surface of the base. The groove may be disposed adjacent the cutting feature to provide a passageway for the bone removed by the cutting feature.

In some configurations, the guide may include a pilot tip extending from the first surface of the base. The guide feature lumen may extend through the guide feature and the pilot tip.

Preparing the bone can include advancing the guide onto a resected surface of the bone, e.g., a humeral bone. Optionally, the guide may be positioned on the resected surface using a pilot tip. The clinician may remove additional bone as the guide is advanced onto the resected surface of the bone or while the guide is on the resected surface of the bone. For example, an osteotome may be advanced through a passageway along a periphery of the guide. A tool, e.g., awl or sounder, may be advanced through a guide feature of the guide and along a medullary canal of the bone.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

The instrumentation and techniques described herein provide a link between the position of the implant stem axis and the position of the proximal bowl/tray to avoid the above-described complications associated with independent diaphysis and metaphysis preparation. The instrumentation allows the surgeon to evaluate the metaphysis and diaphysis and prepare the bone according to the shape of the implant. The instrumentation also provides opportunities to modify the version, if necessary. Although certain instruments and techniques have been described herein in connection with a humeral bone, the instrumentation and techniques described herein can be used with other long bones, including the femur.

Figure 3C:
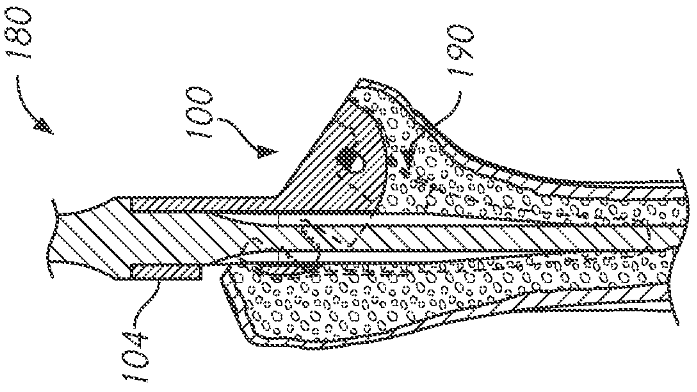
FIGS. 3A-3C illustrate the use of an example of a humeral guide providing a link between the diaphysis axis and the metaphysis axis of the humerus bone.
Figure 3B:
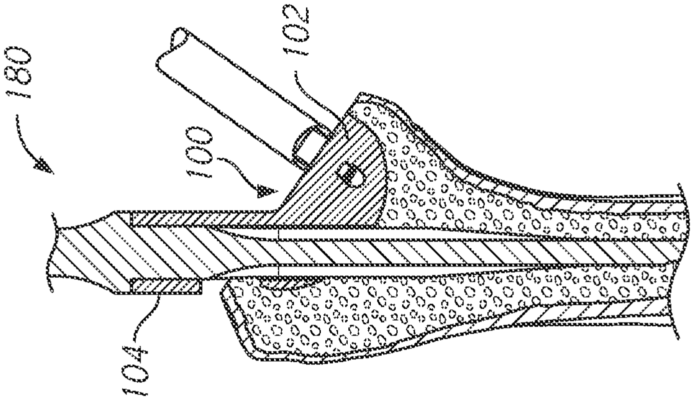
Figure 3A:
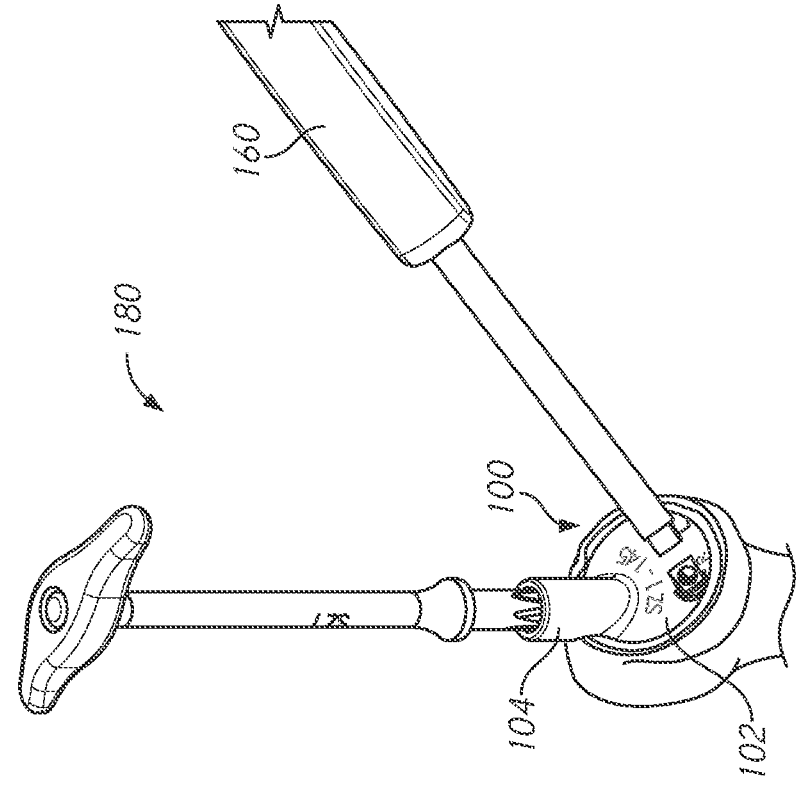

FIGS. 3A and 3B illustrate a humeral guide 100 positioned in a reamed cavity of a metaphysis of a humerus. The base 102 of the humeral guide 100 is centered in the reamed cavity and provides metaphyseal referencing. As shown in FIG. 3B, the humeral guide 100 includes a guide feature 104 to guide the starter awl 180 toward or into a central portion of the canal. FIG. 3C illustrates the relative positions between the starter awl 180 and the final implant 190. As shown, the stem axis of the final implant 190 is aligned with the axis of the starter awl 180, while the implant tray is centered in the reamed cavity. Although this and other humeral guides herein are described in connection with a starter awl, the humeral guides can guide any tool, including different sized awls, sounders, broaches, punches, or other tools.

Figure 4A:
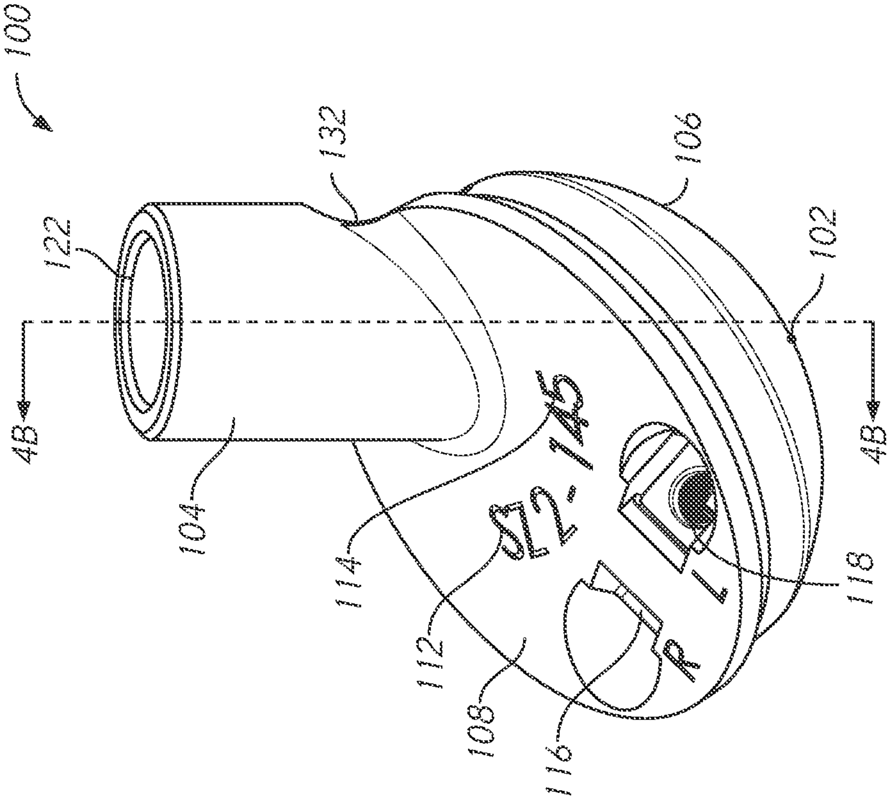
FIGS. 4A and 4B illustrate the humeral guide shown in FIGS. 3A-3C, separate from the humerus bone.

FIG. 4A illustrates the humeral guide 100 shown in FIG. 3A. As discussed above, the humeral guide 100 includes a base 102 and a guide feature 104. The base 102 includes a first or lateral surface 106 configured to contact the metaphysis and a second or medial surface 108 opposite the first surface 106.

The base 102 is configured to be centered within an outer periphery of the metaphysis so that the final implant does not break through a proximal portion of the cortical bone. For example, as shown in FIG. 3B, the curved profile of the first surface 106 enables the base 102 to be positioned within a reamed cavity in the metaphysis. Although, as shown in later examples, the first surface 106 can take on any profile, including planar, conical, cylindrical, or otherwise, depending on how the metaphysis is prepared.

The humeral guide 100 can include an indicator, for example text, color, surface modifications, etc., e.g., a size indicator 112 of a particular size and/or inclination angle indicator 114 of a particular angle of the humeral guide 100. As detailed further below, the humeral guide 100 can form part of a kit including a plurality of humeral guides 100. The humeral guides 100 may vary in size, e.g., diameter, as indicated by the size indicator 112. The size of the humeral guide 100 can mimic the size of the final implant, for example a proximal face of the final implant stem.

The humeral guides 100 may provide different inclination angles between the guide feature 104 and the base 102 as indicated by the inclination angle indicator 114. The inclination angle of the humeral guide 100 can represent a stem inclination angle of the final implant. The humeral stem is usually offered in one fixed inclination angle, e.g., between 125 degrees and 155 degrees. The humeral stem can be configured with a fixed 135 degree inclination angle. The humeral stem can be configured with a fixed 145 degree inclination angle.

The surgeon may prefer to use a handle 160 to position the humeral guide 100 on the anatomy. Accordingly, the second surface 108 can optionally include one or more handle attachment features 116, 118 configured to interface with a modular handle 160 (see FIG. 3A). As shown in FIG. 4A, the humeral guide 100 can include a right handle attachment feature 116 and/or a left handle attachment feature 118, depending on which arm is being prepared, preferences of the surgeon, and/or attachment interface on the handle 160. For example, the right handle attachment feature 116 is accessible through an anterior incision accessing the right arm, while the left handle attachment feature 118 is accessible through an anterior incision accessing the left arm. The handle attachment features 116, 118 can be positioned at an inferior region of the humeral guide 100. For example, each handle attachment feature 116, 118 can be an angled opening on a second surface 108 of the humeral guide 100. Other possible configurations are shown in later examples.

Figure 4B:
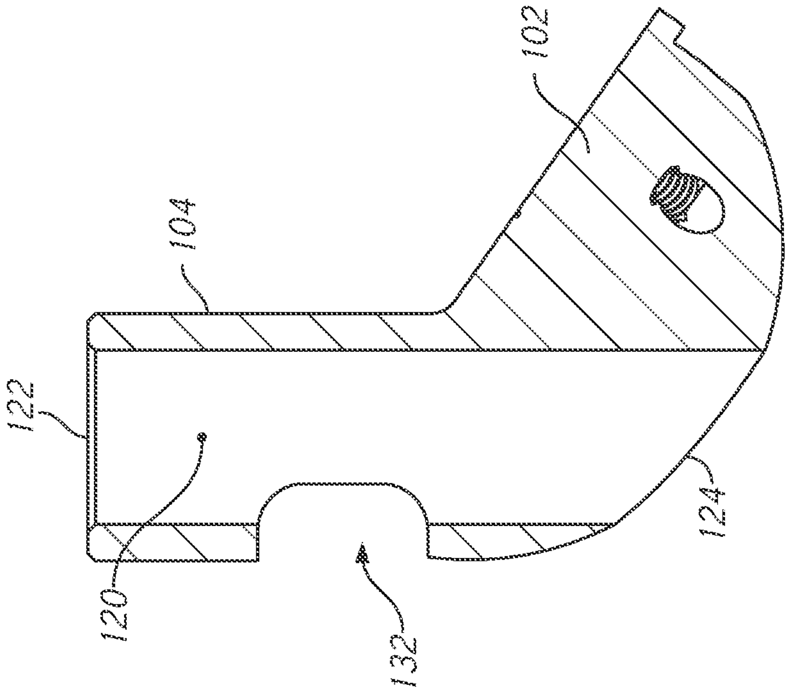

The humeral guide 100 can include a guide feature 104 on or accessible from the second surface 108. As shown in FIG. 4B, the guide feature 104 defines a lumen 120 extending from a proximal opening 122 of the guide feature 104 to a distal opening 124 of the base 102 such that a tool can be advanced through the humeral guide 100. The guide feature 104 is configured to guide a tool into a diaphysis of the humerus bone along a central portion of a canal in the diaphysis. The guide feature 104 can be positioned at a superior side or region of the base 102 so the guide feature 104 can guide a tool into the diaphysis. In this context, superior includes a side of the guide that would be opposite to an inferior portion of the humerus regardless of the orientation of the patient in surgery.

Although not required, the guide feature 104 can extend outwardly from a surface of the base 102 to provide additional stabilization and support for the tool. For example, as shown in FIG. 4A, the guide feature 104 extends away from the second surface 108. The guide feature 104 can have a cylindrical profile. In other configurations, the proximal opening 122 of the guide feature may be positioned at or flush with the second surface 108.

The guide feature 104 can include a relief 132 at a transition between the guide feature 104 and the base 102 to facilitate manufacturing or surgical use. For example, in certain surgical techniques the relief 132 also allows the base 102 to fully sit within the reamed cavity so the guide feature 104 does not obstruct proper positioning of the base 102 (see FIG. 3B).

Figure 5:
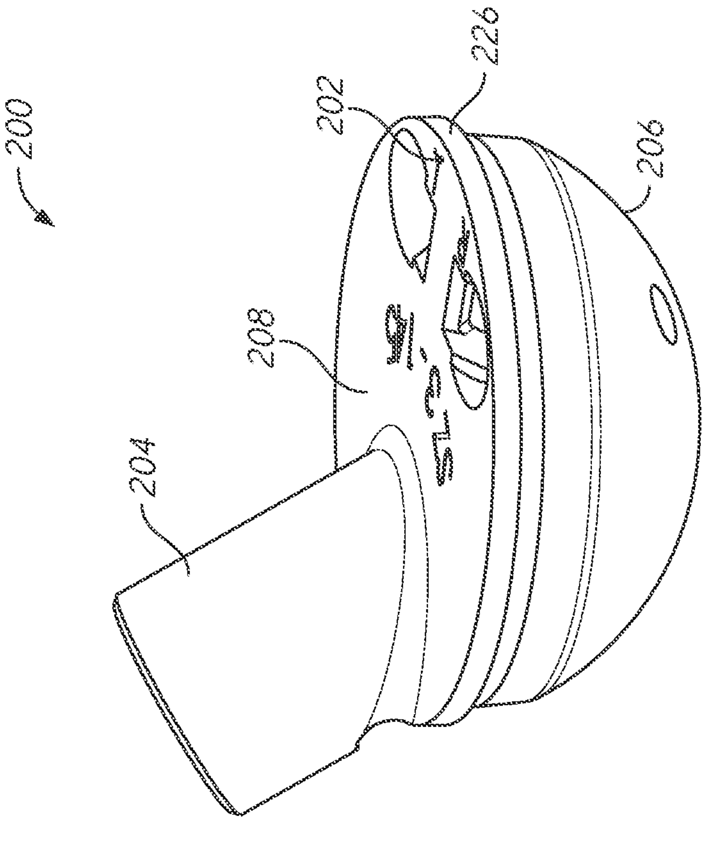
FIG. 5 illustrates another humeral guide including a depth stop collar.

FIG. 5 illustrates another humeral guide 200 that can include any of the features described above with respect to FIGS. 4A and 4B. The humeral guide 200 includes a depth stop 226 configured to control a depth of the humeral guide 200 relative to the bone. In use, the depth stop 226 rests on the resection surface. For example, in certain techniques the humerus is resected, creating a generally planar resection surface. The bone at the resection surface can be altered with a reamer to create a space for the guide 200. The guide can be inserted into the reamed space until the depth stop 226 rests on the resection surface of the humerus around the reamed area. These and related methods are elaborated below. As shown, the depth stop 226 includes a collar that extends transversely, e.g., radially outwardly, from the first surface 206. However, as described in later examples, the depth stop 226 can be a modular component separately attached to a guide that may be otherwise similar to the humeral guide 200.

Figure 6:
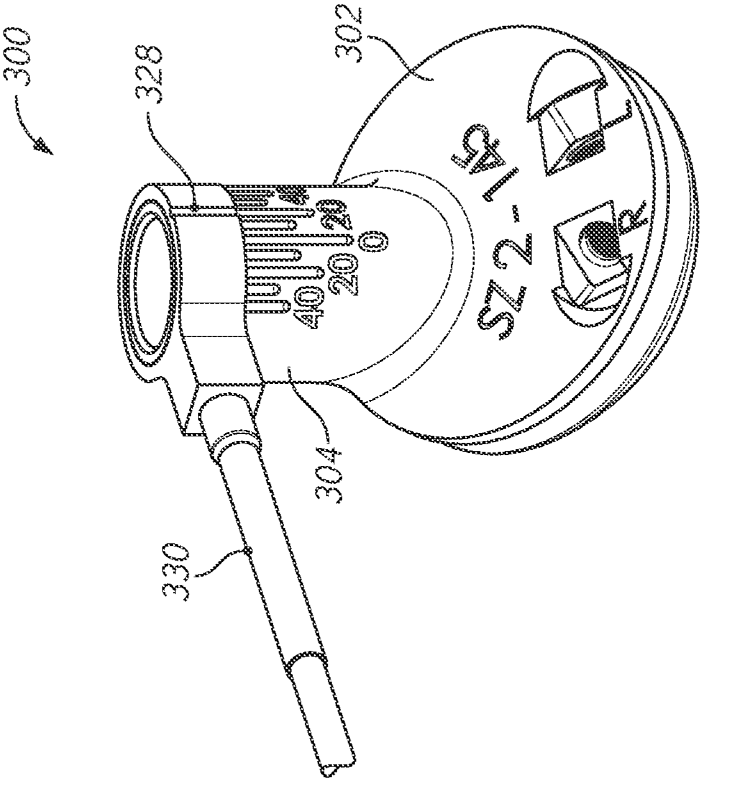
FIG. 6 illustrates another humeral guide including a retroversion indicator.

FIG. 6 illustrates another embodiment of a humeral guide 300 that can include any of the features described above with respect to FIGS. 4A, 4B, and 5. The humeral guide 300 includes a retroversion indicator 328. The humeral guide 300 also includes a retroversion rod 330 to allow the surgeon to evaluate the version. The retroversion rod 330 can be movable relative to the cylindrical body of the guide feature 304. For example, the retroversion rod 330 can be configured to swivel with respect to the retroversion indicator 328. If the proximal humeral resection was not accurate or for other reasons dictated by surgeon's judgement, the surgeon can modify the version by forcing the guide 300 to an appropriate version angle. This technique can also be used to finetune stem access as controlled by the guide 300 as discussed in greater detail below.

Figure 7A:
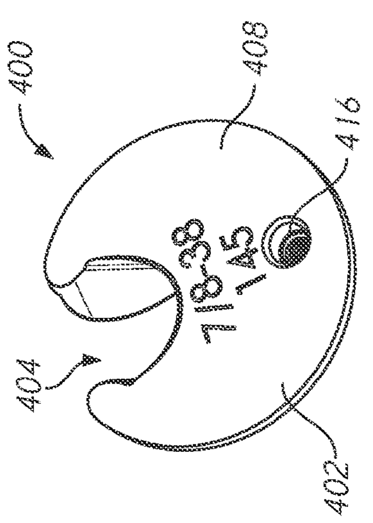
FIGS. 7A-7D illustrate another humeral guide adapted to receive a sounder.
Figure 7B:
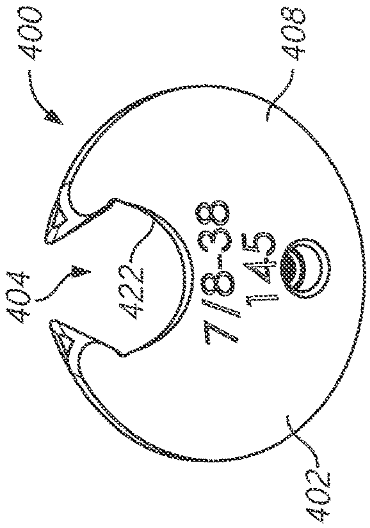
Figure 7C:
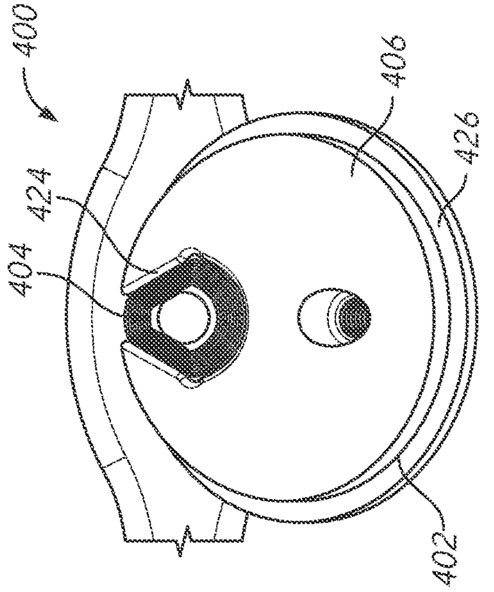
Figure 7D:
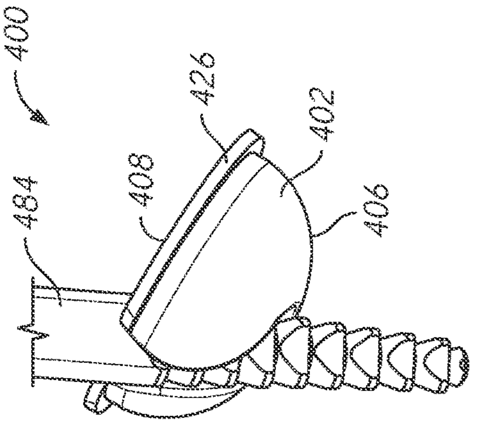

FIGS. 7A-7D illustrate another embodiment of a humeral guide 400 that can include any of the features described above with respect to FIGS. 4A, 4B, 5, and 6. As shown in FIGS. 7C and 7D, the humeral guide 400 can include a base 402 with a first surface 406 and a second surface 408. The second surface 408 can include a depth stop collar 426 extending radially outward beyond the first surface 406. The depth stop collar 426 is configured to rest on the resection surface and control the depth of the humeral guide 400.

The humeral guide 400 can include a guide feature 404 adapted to receive a sounder 484 (see FIG. 7D) or other bone preparation instrument. The guide feature 404 can extend from a proximal opening 422 at the second surface 408 to a distal opening 424 at the first surface 406. The sounder 484 can include a transverse non-circular profile to mimic the shape of the final implant stem. The sounder 484 may be a starter sounder and progressively larger sounders may be used thereafter to enlarge the opening.

The profile of the guide feature 404, for example at the proximal opening 422 and/or at the distal opening 424, can be non-circular and/or shaped to match the sounder 484 or other tool to prevent rotation of the sounder 484. For example, the periphery of the proximal opening 422 can have at least one non-circular portion, e.g., an inflection point where a circular arc joins a linear segment or joins an arcuate section with a different radius of curvature. A portion of the periphery of the proximal opening 422 can be open such that a portion of the sounder or other instrument can be disposed inside the opening 422 and a portion can extend through the side of the periphery out of the opening 422.

The surgeon may prefer to use a handle to position the humeral guide 400 on the anatomy. Accordingly, the second surface 408 can optionally include one or more handle attachment features 416 configured to interface with a modular handle.

Figure 8B:
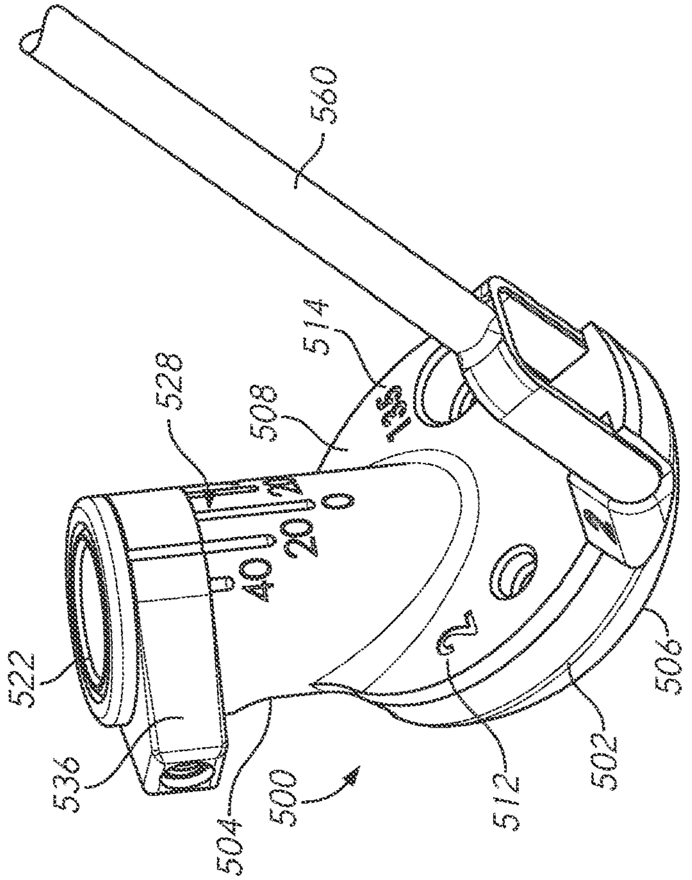
FIGS. 8A-8E illustrate another humeral guide and components thereof.
Figure 8A:
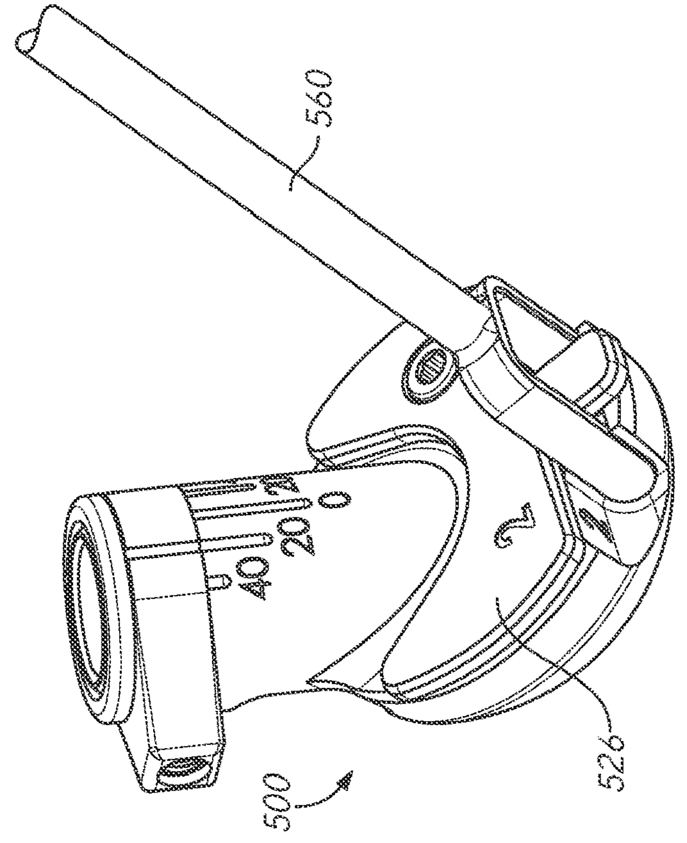
Figure 8D:
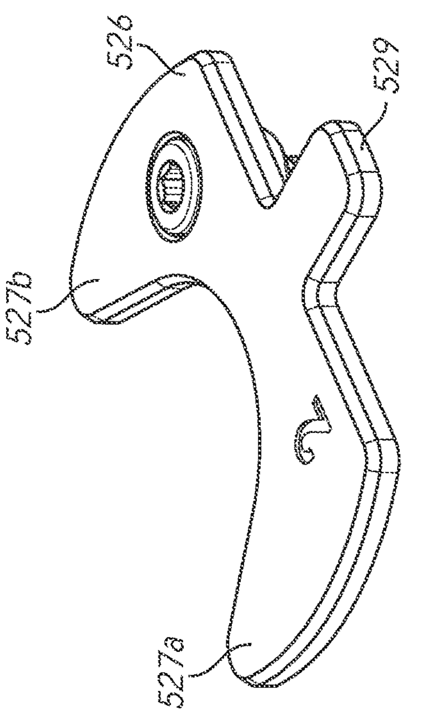
Figure 8E:
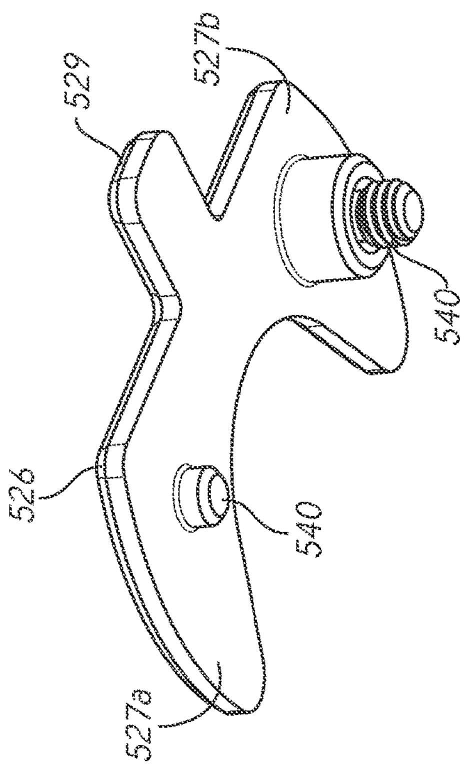
Figure 8C:
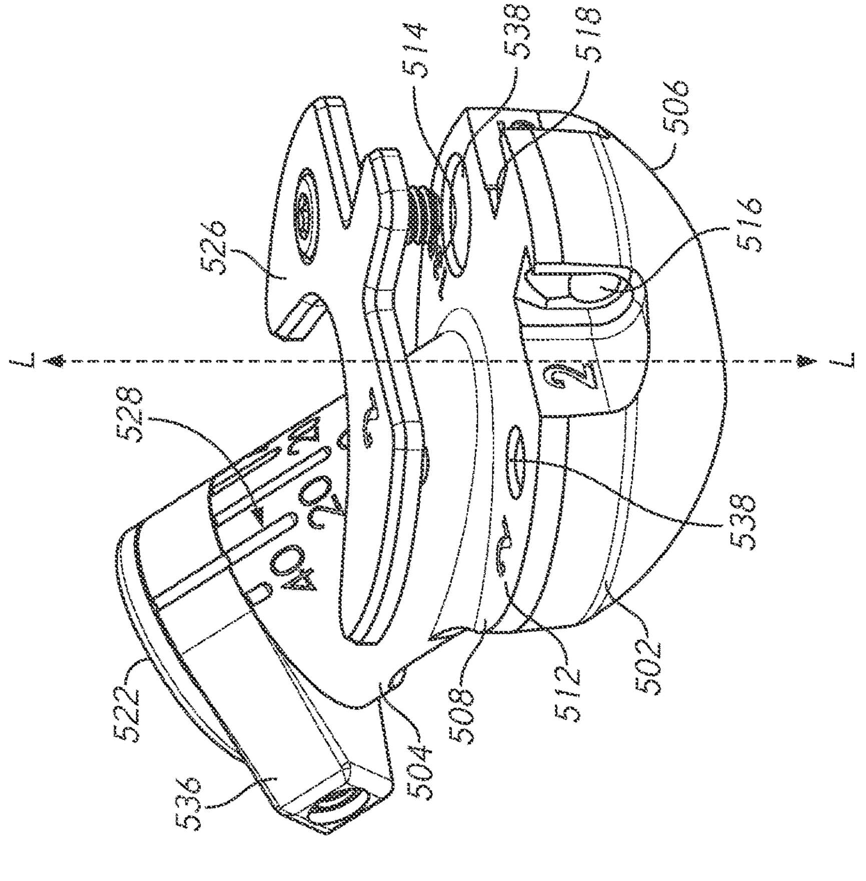

FIGS. 8A-8E illustrate another humeral guide 500 and various components thereof. The humeral guide 500 can include any of the features discussed above with respect to humeral guides 100, 200, 300, and 400. FIG. 8A illustrates the humeral guide 500 configured as an assembly with a modular depth stop 526 and a modular handle 560 attached to a base 502. FIG. 8B illustrates the humeral guide 500 without the modular depth stop 526. FIG. 8C illustrates a partial exploded view of the humeral guide 500 and the modular depth stop 526.

As shown in FIGS. 8B and 8C, the humeral guide 500 includes the base 502 and a guide feature 504. The base 502 includes a first or lateral surface 506 configured to contact the metaphysis and a second or medial surface 508 opposite the first surface 506.

The base 502 is configured to be centered within an outer periphery of the metaphysis so that the final implant which is later to be disposed in the same position as the base 502 does not break through a proximal portion of the cortical bone. As shown, the first surface 506 has a curved profile that enables the base 502 to be positioned within a reamed cavity in the metaphysis. However, the first surface 506 can take on any profile, including planar, conical, cylindrical, or otherwise, depending on how the metaphysis is prepared.

The second surface 508 can include an indicator, for example text, color, surface modifications, etc., e.g., a size indicator 512 of a particular size and/or inclination angle indicator 514 of a particular angle of the humeral guide 500. The size of the humeral guide 500 can mimic the size of the final implant, for example, a proximal face of the final implant stem. The inclination angle can represent a stem inclination angle of the final implant. The humeral stem is usually offered in one fixed inclination angle, e.g., between 125 degrees and 155 degrees. The humeral stem can be configured with a fixed 135 degree inclination angle. The humeral stem can be configured with a fixed 145 degree inclination angle.

The surgeon may prefer to use a handle 560 to position the humeral guide 500 on the anatomy. Accordingly, as shown in the FIG. 8C, the humeral guide 500 can optionally include one or more handle attachment features 516, 518 configured to interface with a modular handle 560. The handle attachment features 516, 518 can be positioned at an inferior region of the humeral guide 500. For example, each handle attachment feature 516, 518 can be an opening extending in a transverse direction or perpendicular to a longitudinal axis L of the humeral guide 500. The handle attachment features 516, 518 can be disposed on a portion of the base 502 opposite to the guide feature 504.

The guide feature 504 of the guide 500 can be disposed on or accessible from the second surface 508. The guide feature 504 defines a lumen extending from a proximal opening 522 of the guide feature 504 to a distal opening of the base 502 such that a tool can be advanced through the humeral guide 500. The guide feature 504 is configured to guide a tool into a diaphysis of the humerus bone along a central portion of a canal in the diaphysis. The guide feature 504 can be positioned at a superior side or region of the base 502 so the guide feature 504 can guide a tool into the diaphysis.

The guide feature 504 can extend proximally from a surface of the base 502 such that the proximal opening 522 is disposed away from (proximal of) the second surface 508 to provide additional stabilization and support for the tool. The guide feature 504 can have a cylindrical profile. The guide feature 504 does not extend proximally in some embodiments.

The guide feature 504 can include a retroversion indicator 528. The humeral guide 500 also can include or be coupled with a retroversion rod to allow the surgeon to evaluate the version. Although the retroversion rod is not shown, the guide feature 504 can include a connector 536 adapted to receive the retroversion rod. The retroversion rod and connector 536 can be moveable relative to the cylindrical body of the guide feature 504. For example, the retroversion rod and connector 536 can be configured to swivel with respect to the retroversion indicator 528. If the proximal humeral resection was not accurate or for other reasons dictated by surgeon judgement, the surgeon can modify the version by forcing the guide 500 to an appropriate version angle. This technique can also be used to fine tune stem access as controlled by the guide 500.

As shown in FIG. 8C, the humeral guide 500 can include a modular stop collar 526 configured to abut or be joined or coupled to the second surface 508 of the base 502. The stop collar 526 can be shaped according to the profile of the second surface 508. For example, the stop collar 526 may at least partially surround a periphery of the guide 500 at or proximal of the second surface 508 and can at least partially surround the guide feature 504 and/or handle attachment features 516, 518 in some embodiments. The stop collar 526 is configured to control a depth of the humeral guide 500 relative to the bone. In use, the stop collar 526 rests on the resection surface defining the position and location of the guide 500 relative to the resection surface. The stop collar 526 has three discrete areas of contact in one embodiment. First and second arcuate segments 527_a_, 527_b_ are provided on opposite sides of the collar 526. A projection 529 of the stop collar 526 disposed between the segments 527_a_, 527_b_ provides contact at a third position. The modular stop collar 526 may be advantageous if the surgeon plans to change the version using the retroversion rod.

The base 502 can include one or more interfacing features 538 adapted to align with and/or join one or more corresponding interfacing features 540 on the stop collar 526. For example, the base interfacing features 538 can include one or more openings on the second surface 508 of the base 502 and the stop collar interfacing features 540 can include one or more projections on an underside of the stop collar 526, or vice versa. Each interfacing feature 538, 540 can be integral with or separate with the base 502 or stop collar 526. Any of the interfacing features 538, 540 can be threaded or include other interlocking features to join the base 502. Any of the interfacing features 538, 540 may not include an interlocking feature and simply provide alignment. As shown in FIG. 8E, the stop collar 526 can include an integral projection with a smooth outer surface and a separate threaded connector for joining the base 502.

Figure 9C:
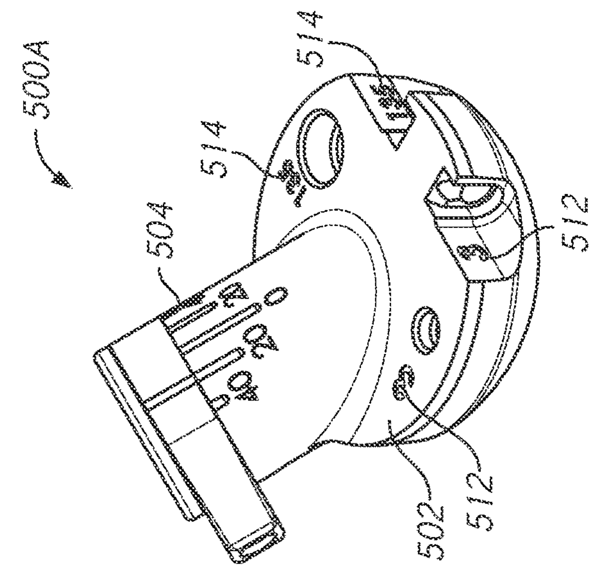
FIGS. 9A-9C illustrate a kit including the humeral guide shown in FIGS. 8A-8E.
Figure 9B:
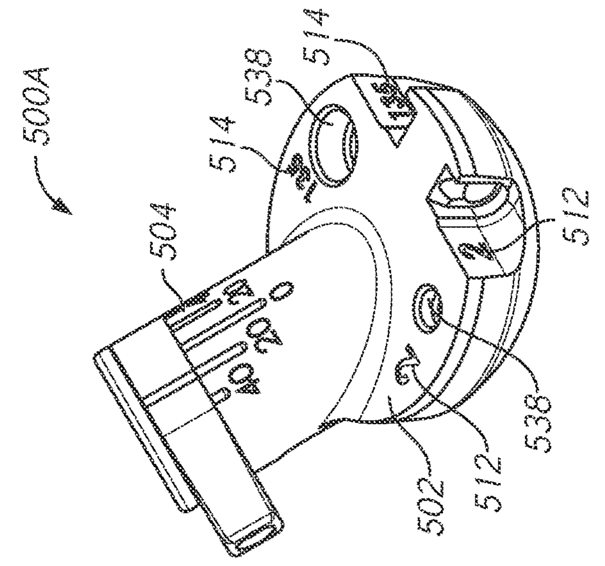
Figure 9A:
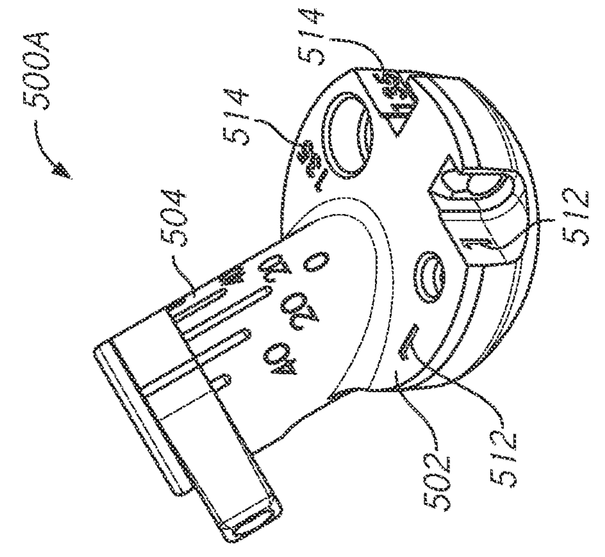

As shown in FIGS. 9A-9C, the humeral guide 500 can form part of a kit including a plurality of humeral guides 500A, 500B, 500C. The humeral guides 500 may vary in size as indicated by the size indicator(s) 512 and/or provide different inclination angles between the guide feature 504 and the base 502 as indicated by the inclination angle indicator(s) 514.

FIGS. 10A-10K illustrate methods of implanting a final implant using the humeral guide 100. These methods can utilize the humeral guides 200, 300, 400, 500 or other humeral guides discussed or covered by the claims herein.

After the surgeon gains access to the humeral head, the superior or proximal end portion of the humerus is resected. The surgeon may be provided with one or more sizing disks 150 to determine a size of the metaphysis, for example, two, three, four, or more different sized disks. For example, each sizing disk 150 can include an arcuate body, e.g., a circular body 166, representative of the diameter of a proximal face of a stem of the final implant 190. The diameter of the circular body 166 may vary between the different sized disks 150. Each sizing disk 150 can include a sizing indicator 112 representative of the size of the sizing disk 150. As described in more detail below, the selected sizing disk 150 can indicate the size of at least some of the tools and/or implants the surgeon should use to prepare the bone.

Figure 10B:
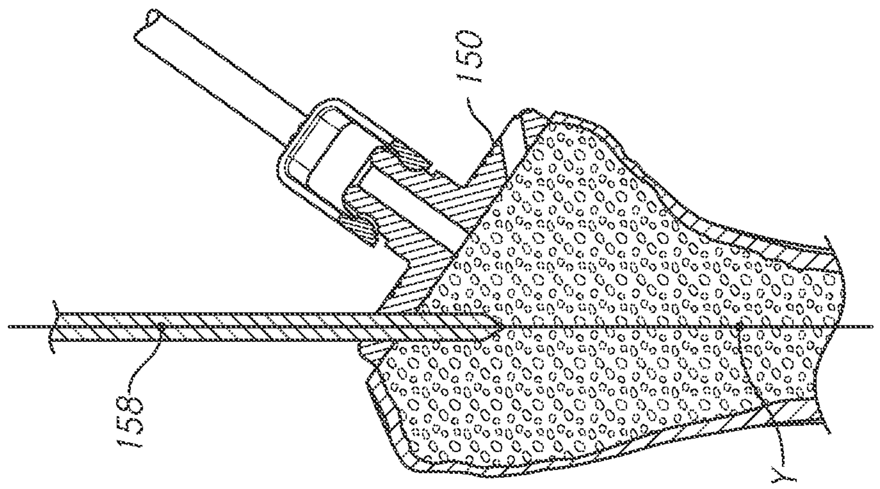
FIGS. 10A-10K illustrate a technique for positioning an implant using the humeral guides shown in at least FIGS. 4A-4B.
Figure 10A:
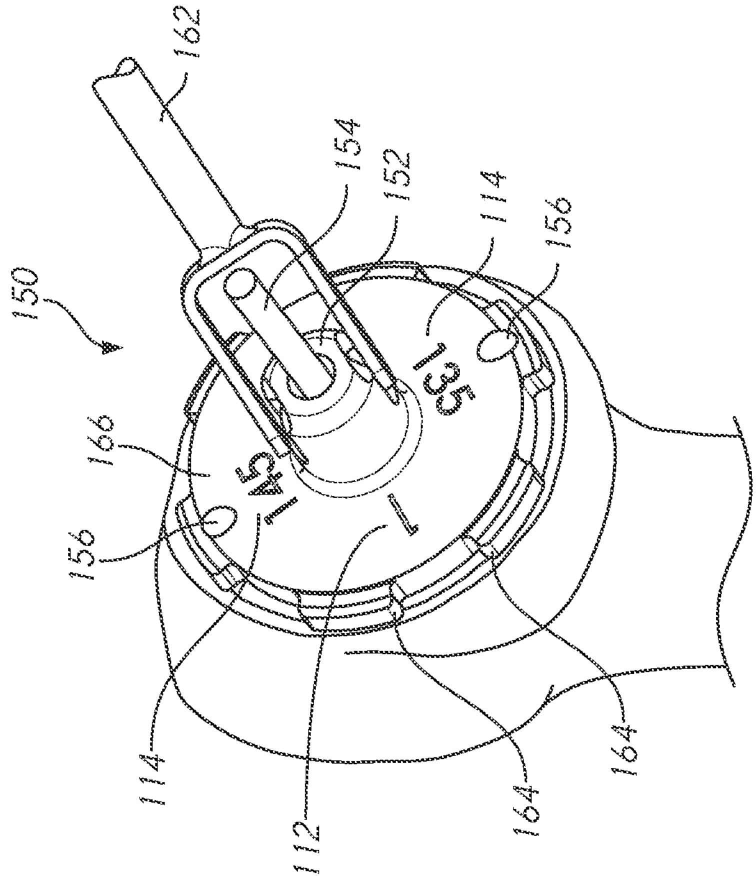

As shown in FIG. 10A, the sizing disks 150 may include one or more tabs 164 or other sizing features extending transversely, e.g., radially outward from the circular body 166. The tabs 164 facilitate visualization of the space between the implant to be implanted (visualized with reference to the circular body 166) and the cortical boundary of the bone. If the outer periphery of the sizing disk 150 hangs over the inner cortical boundary, then the surgeon should select a different sized, e.g., a smaller, sizing disk 150. The thickness of the tabs 164 measured from the circular body 166 to the outer periphery of the tabs 164 can change between the different sizing disks 150.

Optionally, each sizing disk 150 can be positioned using a modular handle 162. The surgeon will select the appropriate sized disk 150 that centers a cannulation hole 152 at the center of the resection surface and fits within the cortical boundary of the resected surface, but does not hang over the periphery of the resected surface (see FIG. 10A). The cannulation hole 152 is configured to receive a central guide pin 154 that subsequently is used to center other humeral preparation instruments.

The sizing disk 150 can also include a plurality of inclination holes 156, for example two, three, four, or more holes, providing a different inclination angle relative to the face of the resection surface. The angle of the inclination holes 156 can be representative of a resection angle or a stem inclination angle, e.g., between an axis extending through a distal end of the stem and an axis extending through a proximal face of the stem, of the final implant. The inclination angle can represent the angle between the metaphyseal bowl and the stem to allow the surgeon to evaluate approximate stem axis position relative to the humeral canal before committing to the bowl placement in the metaphysis.

Each inclination hole 156 can be provided with an inclination indicator 114 that indicates the inclination angle of each inclination hole 156. For example, in FIG. 10A, the inclination hole 156 identified as "145" represents a 145 degree angle relative to the face of the resection surface. The inclination hole 156 identified as "135" represents a 135 degree angle relative to the face of the resection surface. The surgeon can rotate the sizing disk 150 to select the appropriate inclination angle.

Figure 1B:
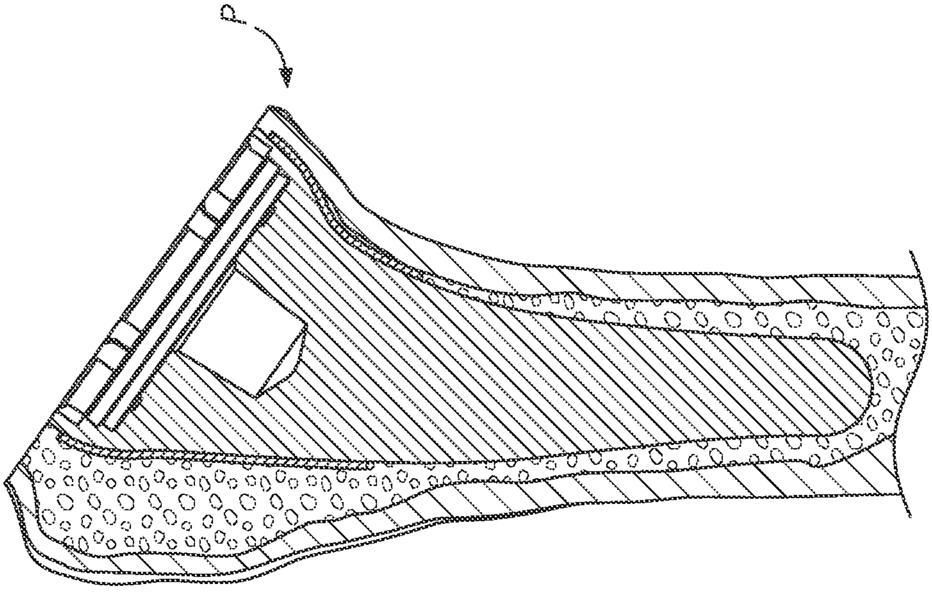
FIGS. 1A-1B illustrate complications from a diaphyseal referencing technique.
Figure 1A:
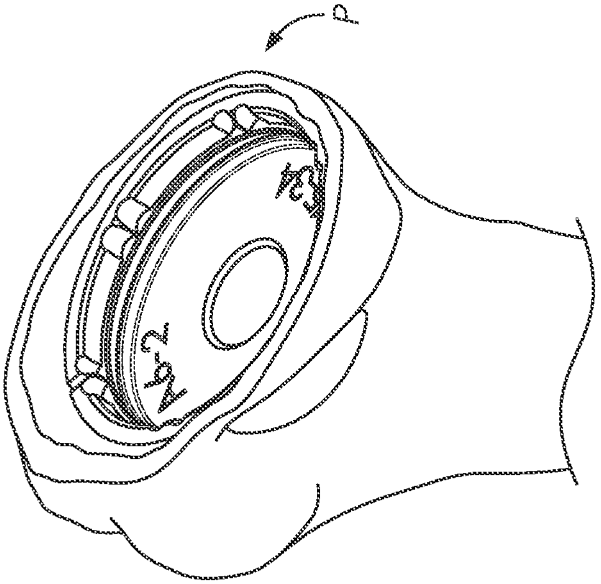
Figure 2B:
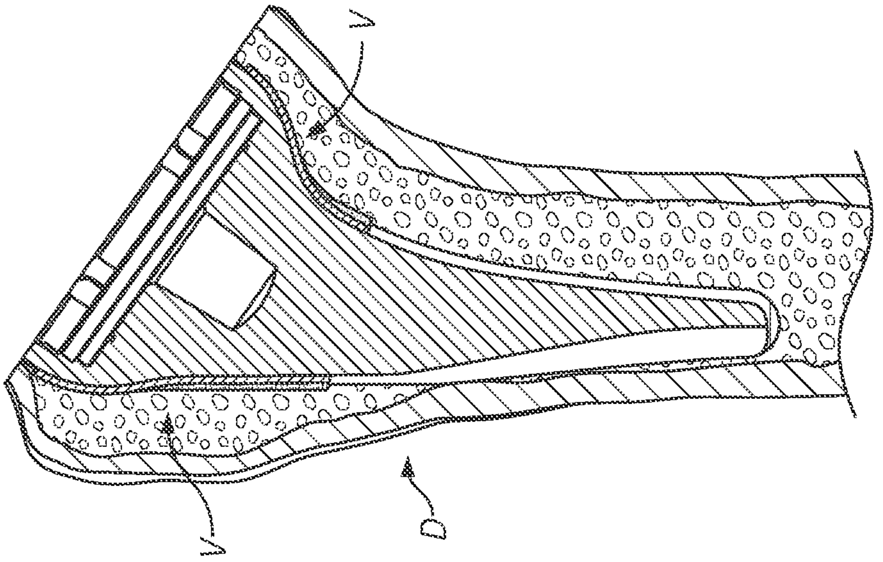
FIGS. 2A-2B illustrate complications from a metaphyseal referencing technique.
Figure 2A:
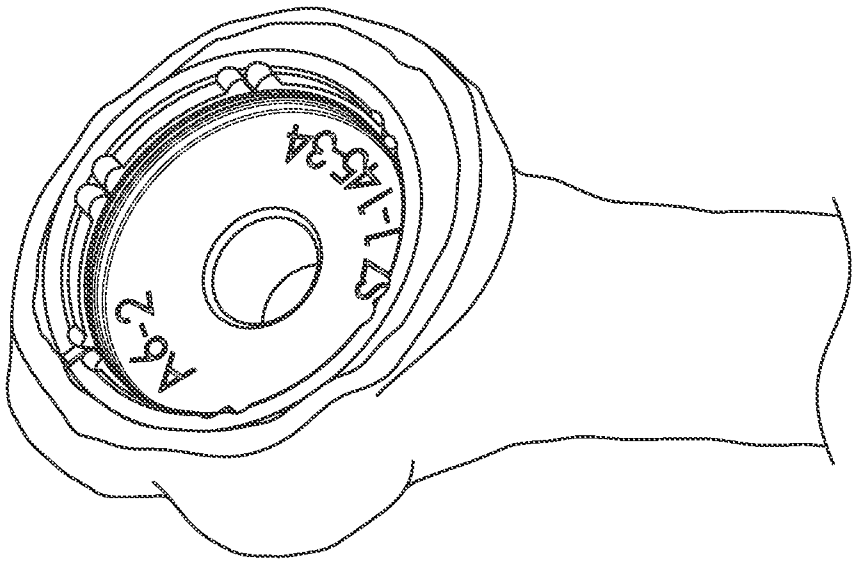

As shown in FIG. 10B, the surgeon can place a pin 158, for example a drill pin, through one of the inclination holes 156 to visualize the location of the pin relative to the diaphysis axis Y. If the pin is displaced from the diaphysis axis Y, for example, superior or lateral to the diaphysis axis Y, the surgeon may select a different sized disk 150 to move the pin 158 closer to the diaphysis axis Y. If the pin 158 and the diaphysis axis Y are misaligned, there is a risk of distal cortical bone impingement (see FIG. 2E). The pin 158 can be placed prior to or after positioning the central guide pin 154. Alternative to the pin, a structure, such as a retroversion indicator, may be integrated with and/or extend from the sizing disk 150 to provide a visual marker.

The sizing disk 150 can also help verify that the angle of the resected surface is appropriate. If the pin 158 is not in line with or parallel the diaphysis axis Y, then the angle of the resected surface may be off and the surgeon can recut the resected surface or make another adjustment to improve the positioning in the humerus.

Figure 10D:
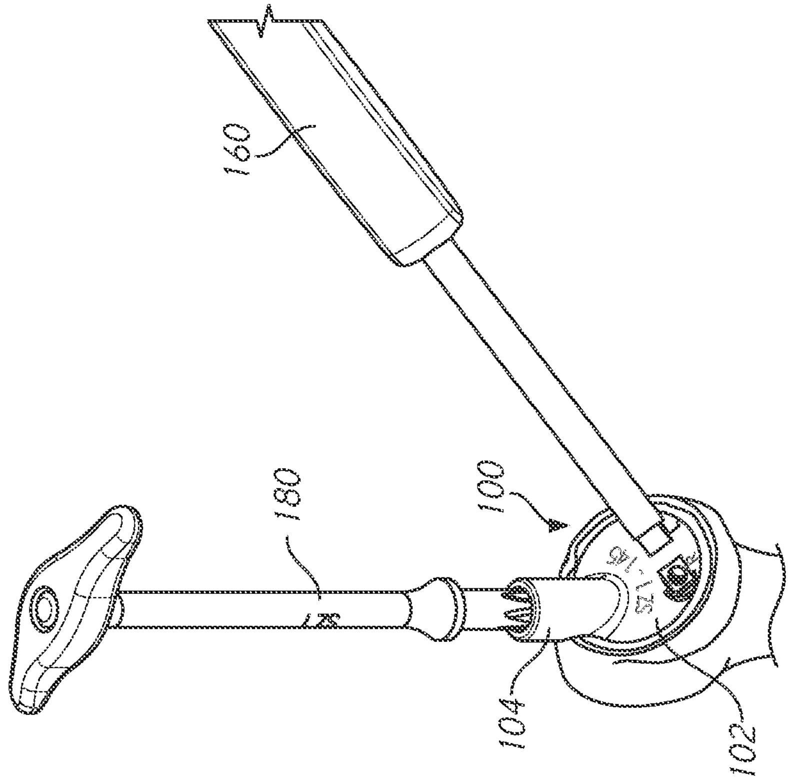
Figure 10C:
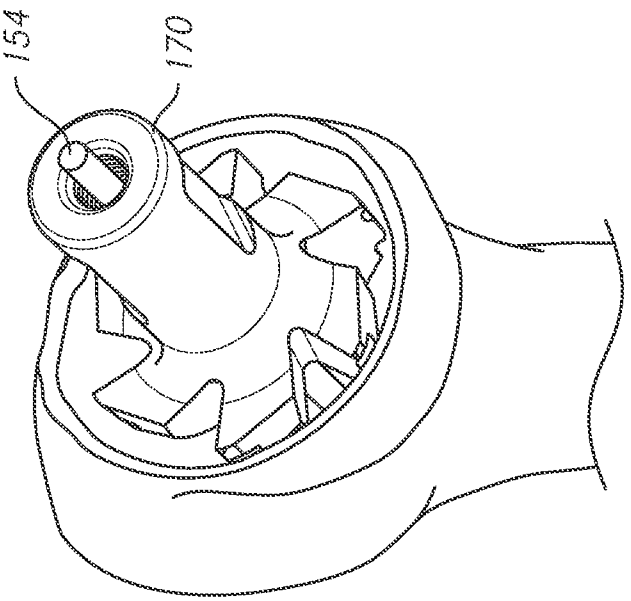

After selecting the appropriate sizing disk 150, a corresponding sized reamer 170 may be selected and delivered over the central guide pin 154 to ream the metaphysis (see FIG. 10C). The reamer 170 produces a generally concave surface in the resected humerus. The surface can generally match the curvature of the first or lateral surface 106, though being an inverse thereof.

After reaming, the first surface 106 of any of the above-described humeral guides may be positioned in the reamed cavity. A humeral guide 100 is selected based on the selected sizing disk 150 and/or selected inclination angle. The diameter of the base 102 corresponds to the diameter of the circular body 166 of the selected sizing disk 150. The orientation of the guide feature 104 corresponds to the selected inclination angle.

The humeral guide 100 may be positioned in the metaphysis using a modular handle 160. As previously discussed with respect to FIG. 3B, the base 102 should be fully seated within the reamed cavity to provide metaphyseal referencing. The relief 132 allows the base 102 to fully sit within the reamed cavity. For example, the transition from the concave reamed surface to the generally planar resection surface of the humerus can be partly received in the relief 132. A starter awl 180 may be selected based on the selected sizing disk 150.

As shown in FIG. 10D, the starter awl 180 is delivered through the guide feature 104 to create a pilot hole in line with the diaphysis axis. The pilot hole may extend toward or through the canal and in some techniques can extend at least the length of the final implant 190. Although not shown, after creating the pilot hole, different sized awls or sounders may be utilized to compact or otherwise prepare bone.

Figure 10E:
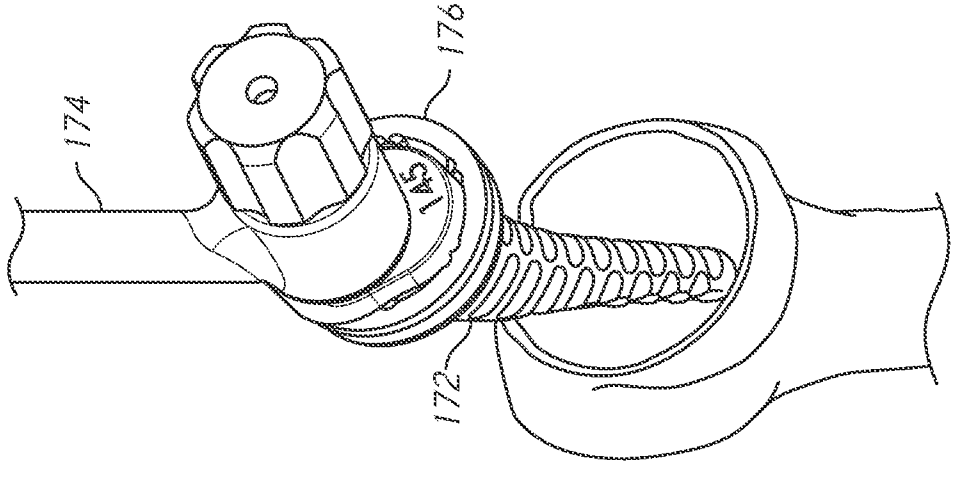

After creating the pilot hole, a compactor 172 may be selected based on the size and shape of the final implant 190. As shown in FIG. 10E, the compactor 172 may be delivered using an inserter handle 174. The tip of the compactor 172 is placed into the pilot hole until the depth stop 176 rests on the resected surface of the humerus around the concave surface formed by reaming, as discussed above. Multiple sized compactors 172 may be utilized to get up to the size of the desired final implant 190.

Figure 10F:
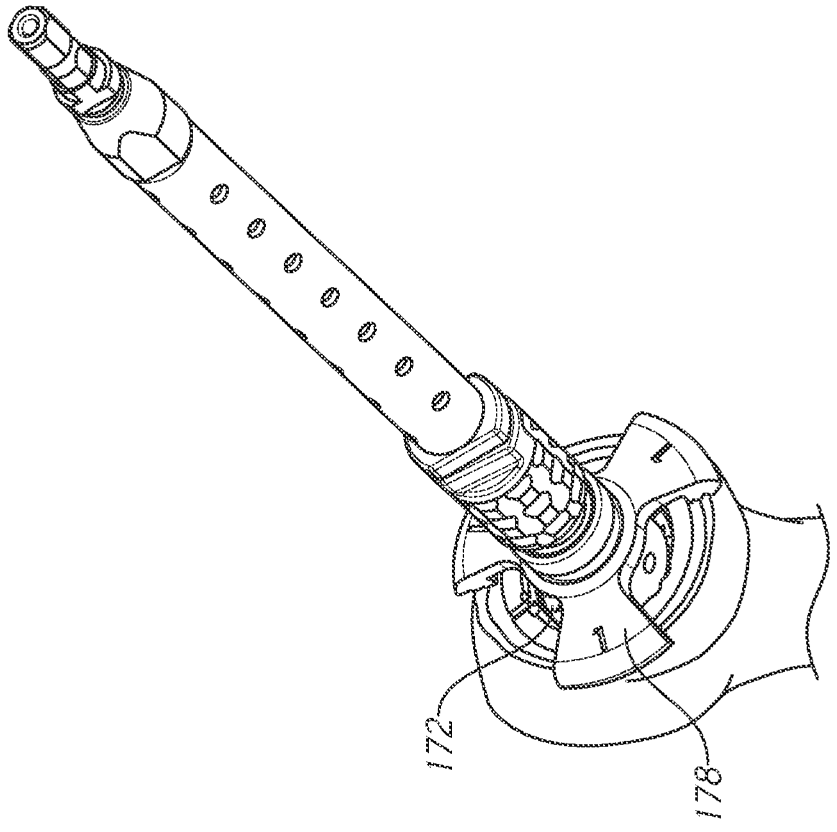
Figure 10G:
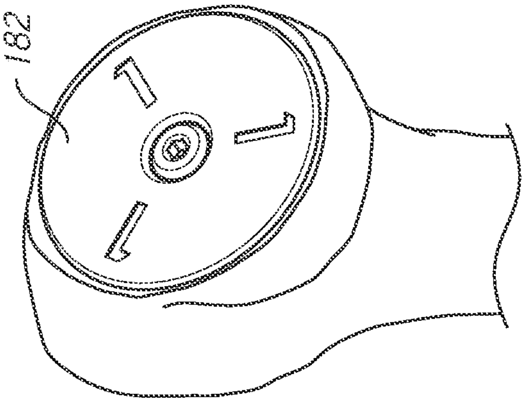
Figure 10I:
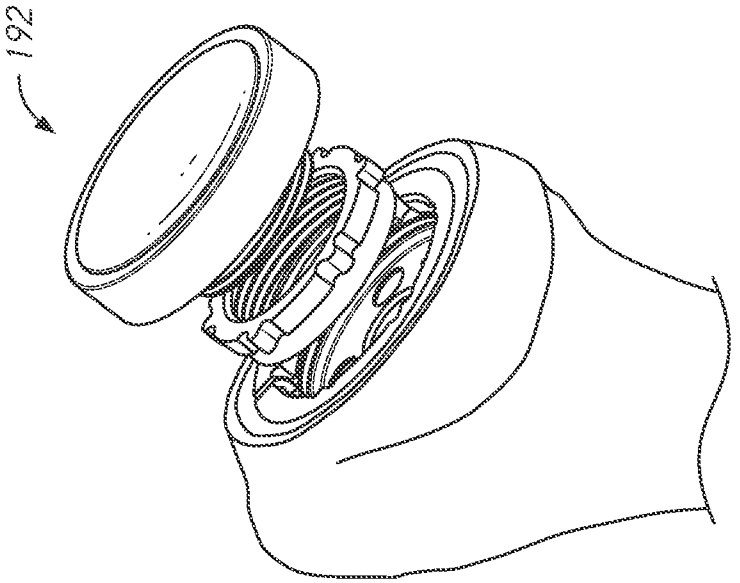
Figure 10H:
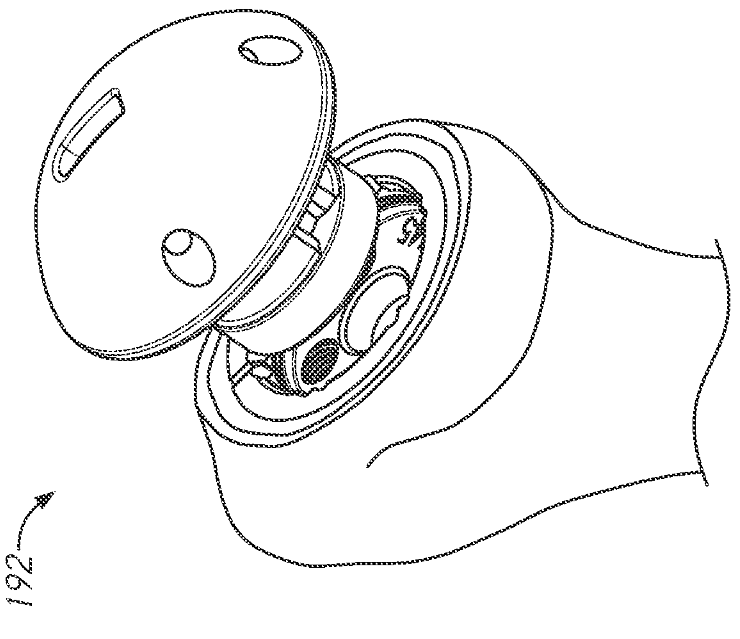
Figure 10K:
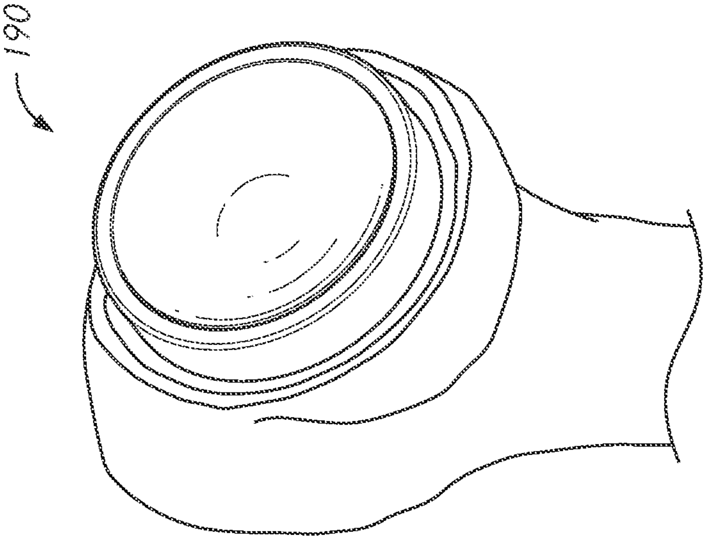
Figure 10J:
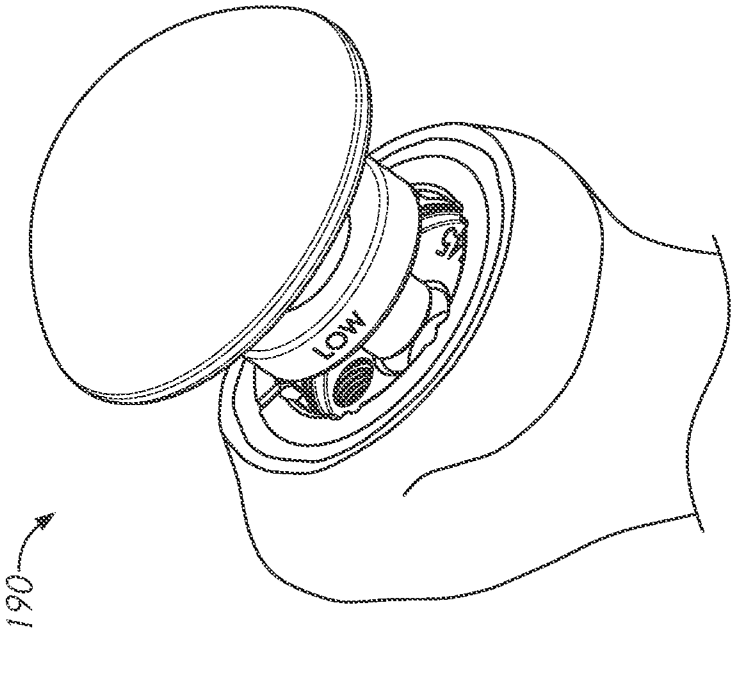

With the compactor 172 in place, a surface planer 178 may be utilized to ensure a flat resection true to the implant (see FIG. 10F). An appropriately sized surface planer 178 may be selected based on the selected sizing disk 150. While preparing the glenoid or during other surgical steps not involving humeral preparation, an appropriately sized cut protector 182 may be provided on the resection surface to protect the resection from retractors. The protector 182 may be selected based on the selected sizing disk 150.

After the humeral bone has been prepared, an anatomical trial implant (FIG. 10H) or a reverse trial implant (FIG. 10I) may be positioned in the humeral bone. Thereafter, the trial implant 192 may be removed, and the final anatomical implant (FIG. 10J) or final reverse implant (FIG. 10K) may be implanted. The final anatomical implant can take any suitable configuration, such as any that are described in Application No. PCT/US2019/054005, titled "SHOULDER PROSTHESIS COMPONENTS AND ASSEMBLIES," and Application No. PCT/US2019/054023, titled "MODULAR HUMERAL HEAD," each of which is hereby incorporated by reference in its entirety herein. The final anatomical implant can take any configuration as disclosed in Application No. 62/908,725, titled "SHOULDER PROSTHESIS COMPONENTS AND ASSEMBLIES," which is hereby incorporated by reference in its entirety herein.

As mentioned above, the surgeon may be provided with an instrumentation kit including a plurality of sizing disks 150 and a plurality of humeral guides 100 (or humeral guides 200, 300, 400, 500). The different components can be designed to transfer the shape of each available final implant to the bone. For example, the kit may include at least three different-sized disks 150. Each sizing disk 150 can include at least two different inclination angles. Thus, the kit can include at least three different sized humeral guides 100. Each humeral guide size can have at least two different guide feature 104 orientations for different inclination angles. Further, each humeral guide size can include a corresponding sized starter awl or other starter tool.

Figure 11:
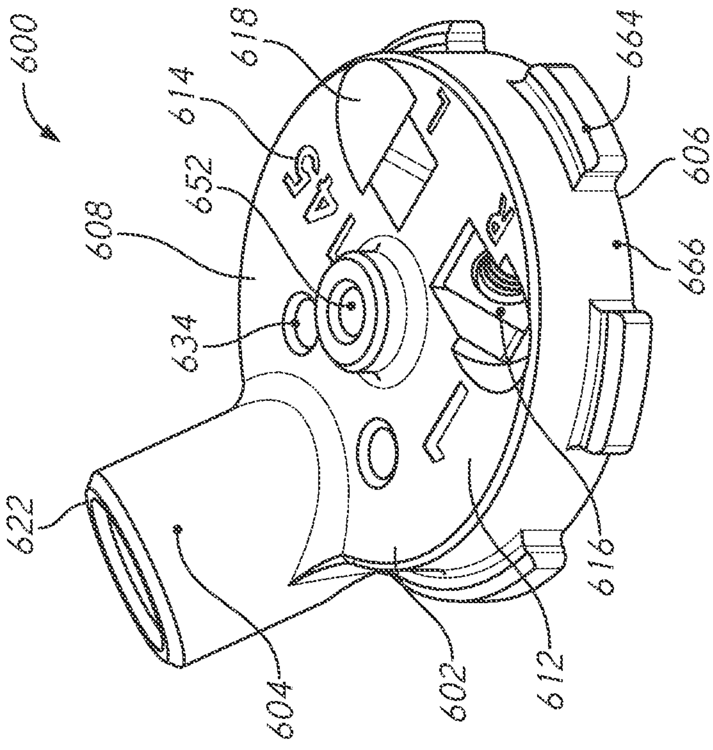
FIG. 11 illustrates another humeral guide including an integrated sizing feature.

FIG. 11 illustrates a humeral guide 600 with integrated sizing features and functions. The humeral guide 600 allows the surgeon to create the pilot hole in the humerus toward or into the medullary canal prior to reaming the metaphysis. Because the humeral guide 600 has integrated metaphyseal sizing, the guide 600 still allows for metaphyseal referencing while forming the pilot hole as part of preparing the diaphysis. The humeral guide 600 can include any of the features described above with respect to humeral guides 100, 200, 300, 400, and 500.

As discussed above, the humeral guide 600 includes a base 602 and a guide feature 604. The base 602 includes a first or lateral surface 606 configured to contact the metaphysis and a second or medial surface 608 opposite the first surface 606.

As shown in FIG. 11, the first surface 606 has a planar profile or configuration. As described in greater detail below, the humeral guide 600 is positioned on the bone after the superior or proximal end portion of the humerus is resected, but before the resected surface is reamed. Thus, the first surface 606 can be formed on or can be disposed in a single plane.

The second surface 608 can include an indicator, for example text, color, surface modifications, etc., e.g., a size indicator 612 of a particular size and/or inclination angle indicator 614 of a particular angle of the humeral guide 600.

As detailed further below, the humeral guide 600 can form part of a kit including a plurality of humeral guides 600. The humeral guides 600 may vary in size as indicated by the size indicator 612 and/or provide different inclination angles between the guide feature 604 and the base 602 as indicated by the inclination angle indicator 614. The inclination angle can be representative of a resection angle or a stem inclination angle, e.g., between an axis extending through a distal end of the stem and an axis extending through a proximal face of the stem, of the final implant. The inclination angle can provide the angle between the metaphyseal bowl and the stem. As shown, the humeral guide 600 has an inclination angle of 145 degrees, but the humeral guide 600 may have other inclination angles, for example between 125 degrees and 155 degrees, e.g., 135 degrees.

The base 602 is configured to be centered within an outer periphery of the metaphysis so that the final implant centered on the same portion of the resected humerus upon which the base 602 is centered, in use, does not break through a proximal portion of the cortical bone. The humeral guide 600 can include an arcuate body, e.g., a circular body 666, representative of the diameter or major axis of a proximal face of a stem of the final implant 190 to be located at the resection plane of the humerus (see FIG. 3C). The diameter of the circular body 666 may vary between the different sized humeral guides 600. Each humeral guide 600 can include a sizing indicator 612 representative of the size of the humeral guide 600. As described in more detail below, the selected humeral guide 600 can indicate the size of at least some of the tools the surgeon should use to prepare the bone.

As shown in FIG. 11, the humeral guide 600 may include one or more tabs 664 or other sizing features extending transversely, e.g., radially outward from the circular body 666. The tabs 664 can be radial projections formed on or extending from a circumferential surface of the guide 600. The projections can extend to a free end. The radial length of the tabs between the circumferential surface and the free end can be indicative of size, as discussed below. The tabs 664 facilitate visualization of the space between the implant to be implanted (visualized with reference to the circular body 666) and the cortical boundary of the bone. If the outer periphery of the humeral guide 600 hangs over the inner cortical boundary, then the surgeon should select a different sized, e.g., a smaller, humeral guide 600. The thickness (also referred to herein as radial length) of the tabs 664 measured from the circular body 666 to the outer periphery of the tabs 664 can change between the different humeral guides 600.

The surgeon may prefer to use a handle to position the humeral guide 600 on the anatomy. Accordingly, the second surface 608 can optionally include one or more handle attachment features 616, 618 configured to interface with a modular handle. As shown in FIG. 11, the humeral guide 100 can include a right handle attachment feature 616 and a left handle attachment feature 618, depending on the arm being prepared, preferences of the surgeon, and/or or attachment interface on the handle. For example, the right handle attachment feature 116 is accessible through an anterior incision accessing the right arm, while the left handle attachment feature 118 is accessible through an anterior incision accessing the left arm. The handle attachment features 616, 618 can be positioned at an inferior region of the humeral guide 600. For example, each handle attachment feature 616, 618 can be an angled opening on a second surface 608 of the humeral guide 600.

The guide feature 604 of the humeral guide 600 can be disposed on or accessible from the second surface 608. The guide feature 604 defines a lumen extending from a proximal opening 622 of the guide feature 604 to a distal opening of the base 602 such that a tool can be advanced through the humeral guide 600. The guide feature 604 is configured to guide a tool into a diaphysis of the humerus bone along a central portion of a canal in the diaphysis. The guide feature 604 can be positioned at a superior side or region of the base 602 so the guide feature 604 can guide a tool into the diaphysis.

Although not required, the guide feature 604 can extend outwardly from (proximally or medially of) a surface of the base 602 to provide additional stabilization and support for the tool. For example, as shown in FIG. 11, the guide feature 604 extends away from the second surface 608. The guide feature 604 can have a cylindrical profile. In other configurations, the proximal opening 622 of the guide feature may be positioned at or flush with the second surface 608.

Any of the guides or sizing disks described herein can include one or more stabilization features, such as stabilization holes 634 extending through the base 602 or barbs or other anchors on the first surface 606. One or more stabilization pins can be driven through a respective stabilization hole 634 to hold the guide 600 in place during diaphyseal preparation. As shown in FIG. 11, the one or more stabilization holes 634 can be offset from the center of the guide 600 and/or positioned at an oblique angle away from the central axis of the base 602 or canal, so the stabilization pins do not obstruct the tool being delivered through the guide 604. After a pilot hole is created in line with the diaphysis axis, a central guide pin can be driven through a cannulation hole 652 to guide other instruments.

FIGS. 12A-12D illustrate a method of implanting a final implant using the humeral guide 600.

After the surgeon gains access to the humeral head, the superior or proximal end portion of the humerus is resected. The surgeon may be provided with one or more humeral guides 600 to determine a size of the metaphysis and evaluate the diaphysis, for example, two, three, four, or more different sized humeral guides. As explained above, each humeral guide 600 can include an arcuate body, e.g., a circular body 666, representative of the diameter of a proximal face of a stem of the final implant 190. Each humeral guide 600 can also include one or more sizing features (e.g., tabs 664) to facilitate visualization of the space between the implant to be implanted (visualized with reference to the circular body 666) and the cortical boundary of the bone. The selected humeral guide 600 can indicate the size of at least some of the tools and/or implants the surgeon should use to prepare the bone.

Figure 12B:
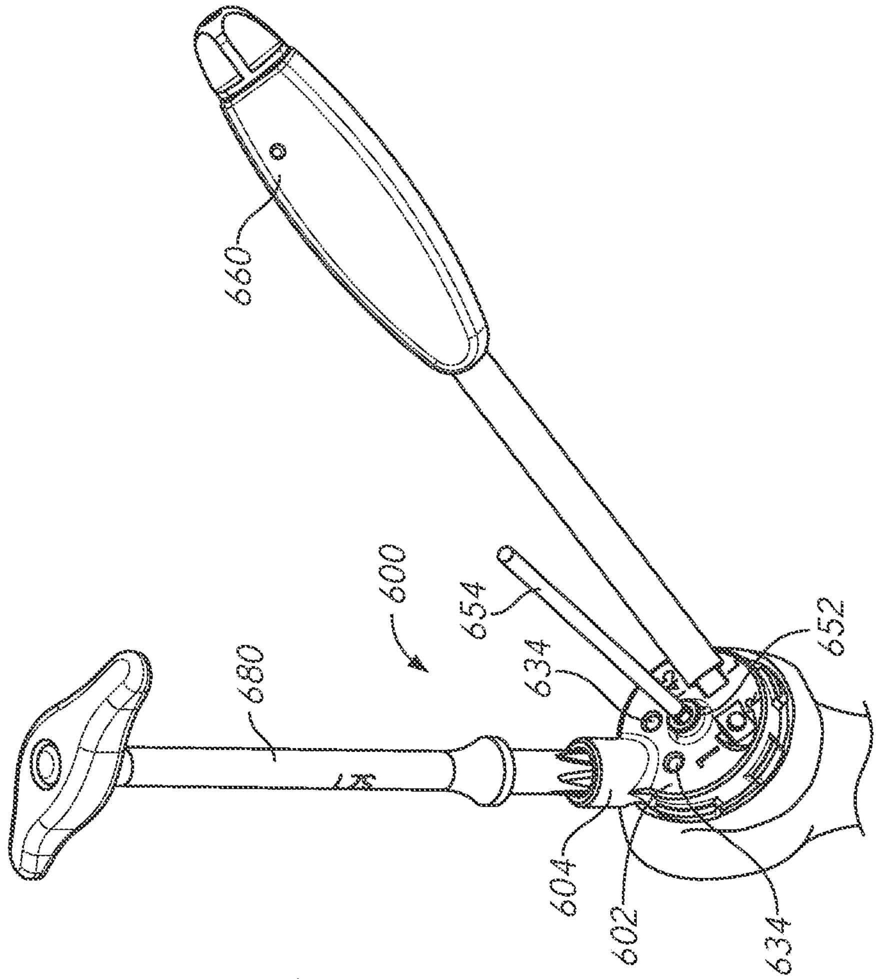
FIGS. 12A-12D illustrate a technique for positioning an implant using the humeral guide shown in FIG. 11.
Figure 12A:
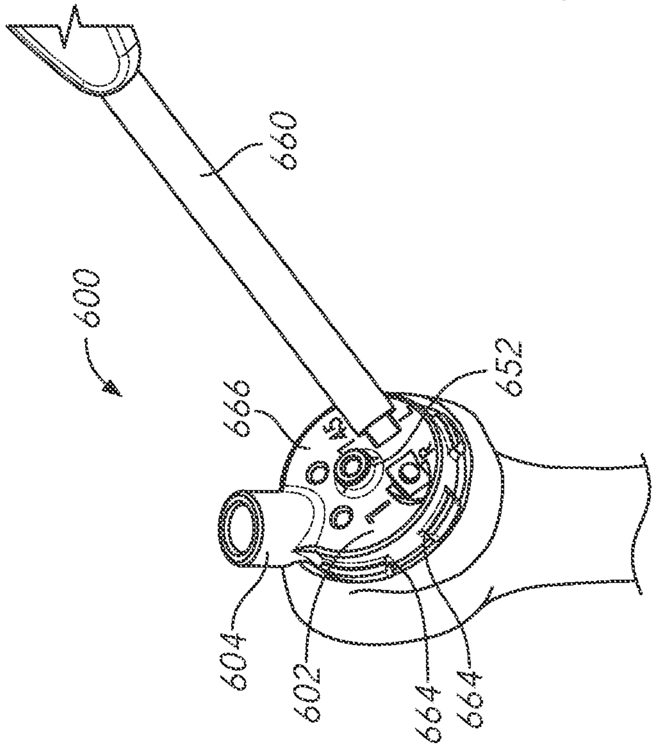

As shown in FIG. 12A, optionally, each humeral guide 600 can be positioned using a modular handle 660. The surgeon will select the appropriate humeral guide 600 that centers a cannulation hole 652 at the center of the resection surface and fits within the cortical boundary of the resected surface, but does not hang over the periphery of the resected surface. The cannulation hole 652 is configured to receive a central guide pin 654 that subsequently is used to center other humeral preparation instruments (see FIG. 12B).

Within each size, the surgeon may be provided with or may select one or more humeral guides 600 having different inclination angles, which can represent an angle relative to the face of the resection surface or the stem inclination angle of the final implant stem to be implanted. The inclination angle allows the surgeon to evaluate approximate stem axis position relative to the humeral canal before committing to the bowl placement in the metaphysis. The cylindrical extension of the guide feature 604 can provide a visual indicator of the inclination angle to help the surgeon select the appropriate inclination angle and/or verify that the angle of the resected surface is appropriate. If the cylindrical extension of the guide feature 604 is not in line with or parallel the diaphysis axis Y, then the angle of the resected surface may be off and the surgeon can recut the resected surface or make another adjustment to improve the positioning in the humerus.

After selecting the appropriate humeral guide 600, optionally, one or more stabilization pins can be driven through a respective stabilization hole 634 to hold the guide 600 in place during diaphyseal preparation. The starter awl 680 or other tool is delivered through the guide feature 604 to create a pilot hole in line with the diaphysis axis. The pilot hole may extend toward or through the canal and in some techniques can extend at least the length of the final implant 190. Although not shown, after creating the pilot hole, different sized awls or sounders may be utilized to compact or otherwise prepare bone. At any time, for example after the pilot hole is created, the central guide pin 654 may be driven through the cannulation hole 652 to guide other instruments.

Figure 12D:
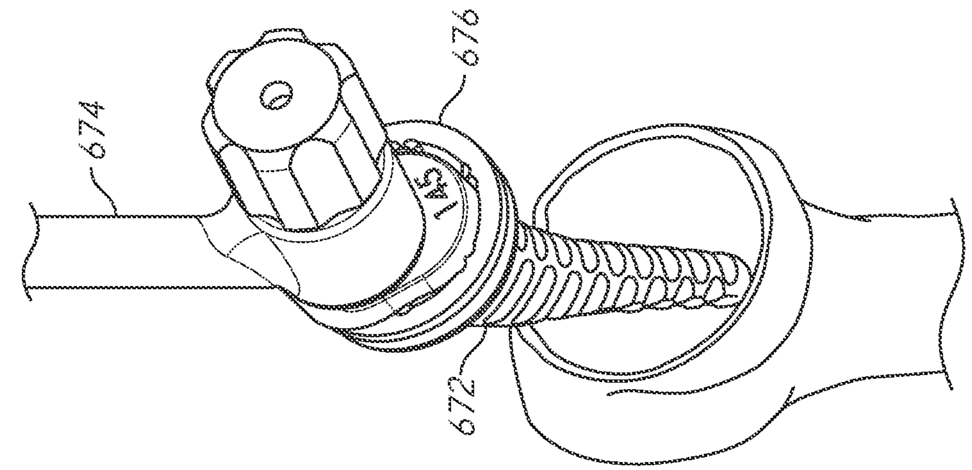
Figure 12C:
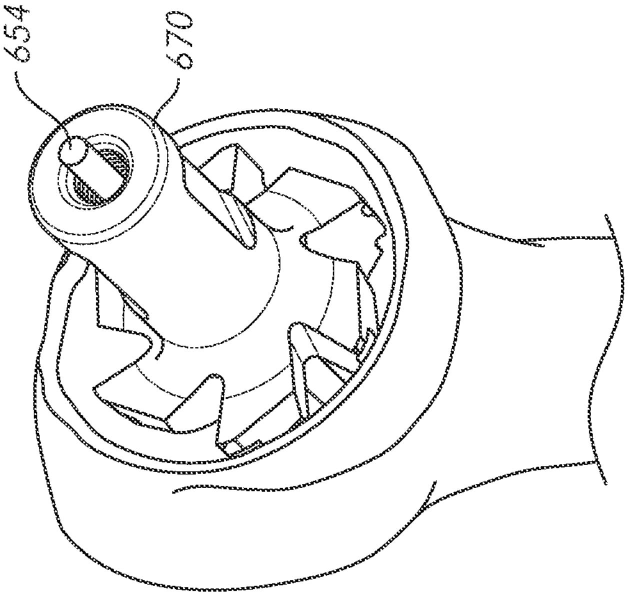

After creating the pilot hole, a corresponding sized reamer 670 may be selected and delivered over the central guide pin 654 to ream the metaphysis (see FIG. 12C). After reaming, a compactor 672 may be selected based on the size and shape of the final implant. As shown in FIG. 12D, the compactor 672 may be delivered using an inserter handle 674. The tip of the compactor 672 is placed into the pilot hole until the depth stop 676 rests on the resected surface of the humerus around the concave surface formed by reaming, as discussed above. Multiple sized compactors 672 may be utilized to get up to the size of the desired final implant.

Following compacting, the same preparation steps described above with respect to FIGS. 10F-10K may be utilized.

Any of the guides described herein may have a patient specific design that matches the metaphyseal and diaphyseal axes of the patient's bone. The guides can be generated based on pre-operative or intra-operative imaging, such as CT scan, MRI scan, X-ray, or other imaging, and formed utilizing, for example, 3-D printing technology or the like.

Figure 13A:
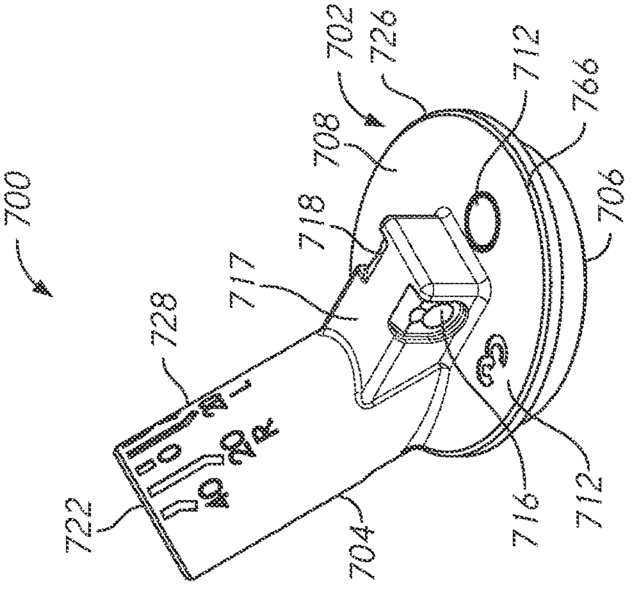
FIGS. 13A-13C illustrate another humeral guide.
Figure 13B:
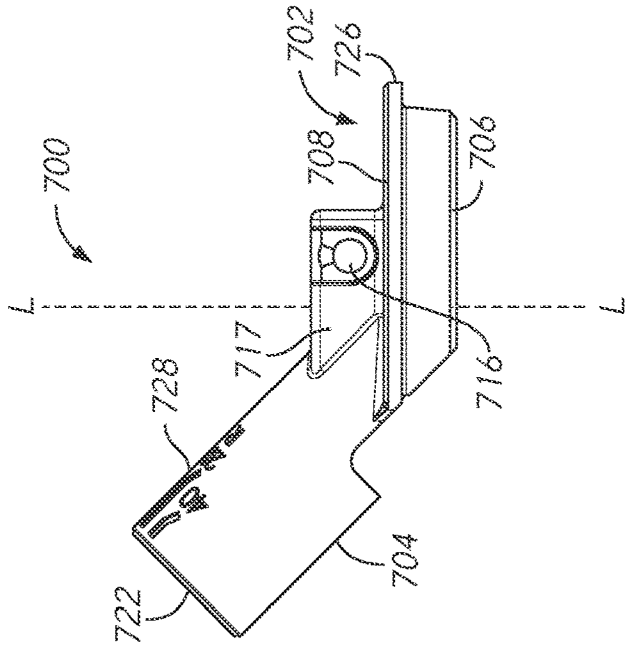
Figure 13C:
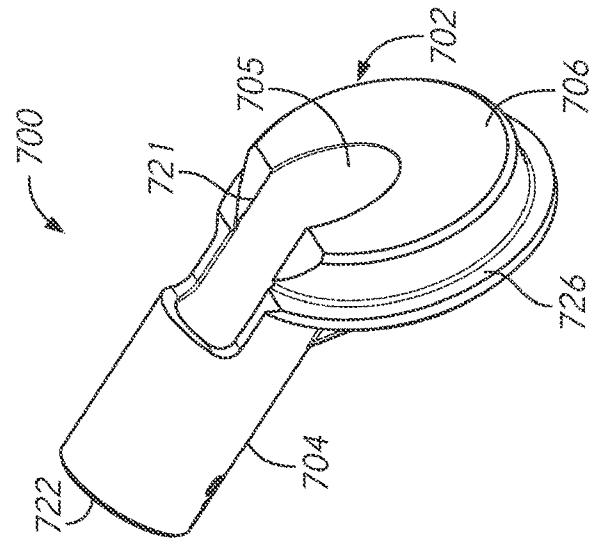

FIGS. 13A-13C illustrate another humeral guide 700. The humeral guide 700 can include any of the features discussed above with respect to any one or more of humeral guides 100, 200, 300, 400, 500, and 600.

As shown in FIGS. 13A-13C, the humeral guide 700 includes the base 702 and a guide feature 704. The base 702 includes a first or lateral surface 706 configured to contact the metaphysis and a second or medial surface 708 opposite the first surface 706. The first surface 706 has a planar profile or configuration (see FIG. 13C). However, the first surface 706 can take on any profile, including spherical, tiered, conical, cylindrical, or otherwise, for example depending on how the metaphysis is prepared.

The second surface 708 can include one or more indicators, for example text, color, surface modifications, etc., e.g., a size indicator of a particular size and/or inclination angle indicator of a particular angle of the humeral guide 700. As shown in FIG. 13A, the humeral guide 700 may include two different size indicators 712, e.g., a text indicator and a color indicator.

The base 702 is configured to be centered within an outer periphery of the metaphysis so that the final implant at least partially centered on the same portion of the resected humerus upon which the base 702 is centered, in use, does not break through a proximal portion of the cortical bone. The humeral guide 700 can include an arcuate body, e.g., a circular or partial circular body 766, representative of the diameter or major axis of a proximal face of a stemmed or stemless anchor of the final implant 190 to be located at or adjacent to resection plane of the humerus (see FIG. 3C). The diameter of the circular body 766 may vary between the different sized humeral guides 700.

The humeral guide 700 may include a depth stop 726 configured to control a depth of the humeral guide 700 relative to the bone. The shape and/or size of the depth stop 726 may correspond to the shape and/or size of a collar on the final implant. The second surface 708 may have a greater diameter and project radially outward of the first surface 706, thus forming the depth stop 726. However, as described in earlier examples, the depth stop 726 can be a modular component separately attached to a guide. As explained further below, the depth stop 726 rests on a recessed surface in the bone in some techniques.

The guide feature 704 of the humeral guide 700 can be disposed on or accessible from the second surface 708. The guide feature 704 defines a lumen extending from a second opening 722 of the guide feature 704 to a first opening 705 of the base 702 such that a tool can be advanced through the humeral guide 700 (see FIG. 14). A rear side of the humeral guide may include an open channel 721 from the guide feature lumen to the first opening 705. The open channel 721 prevents the guide feature 704 from impinging on the resection. Although not required, the guide feature 704 can extend outwardly from (laterally of) a surface of the base 702 to provide additional stabilization and support for the tool. The guide feature 704 can have a cylindrical profile. In other configurations, the second opening 722 of the guide feature 704 may be positioned at or flush with the second surface 708.

The guide feature 704 is configured to guide a tool into a diaphysis of the humerus bone along a central portion of a canal in the diaphysis. The guide feature 704 can be positioned at a superior side or region of the base 702 so the guide feature 704 can guide a tool into the diaphysis.

The humeral guide 700 may also include a retroversion indicator 728, for example on the guide feature 704. As the retroversion rod 730 on the awl 780 is moved relative to the guide feature 704, the retroversion rod 730 allows the surgeon to evaluate the version (see FIG. 14). For example, when the retroversion rod 730 is pointed toward a patient's elbow and parallel with a long axis of the forearm, the position of the indicator 781 on the awl 780 relative to the retroversion indicator 728 provides information on the version. If the proximal humeral resection was not accurate (for example, if the indicator 781 is entirely offset from the retroversion indicator 728) or for other reasons dictated by surgeon judgement, the surgeon can modify the version by adjusting the guide 700 to an appropriate version angle. This technique can also be used to fine tune stem access as controlled by the guide 700 as discussed above.

Figure 16B:
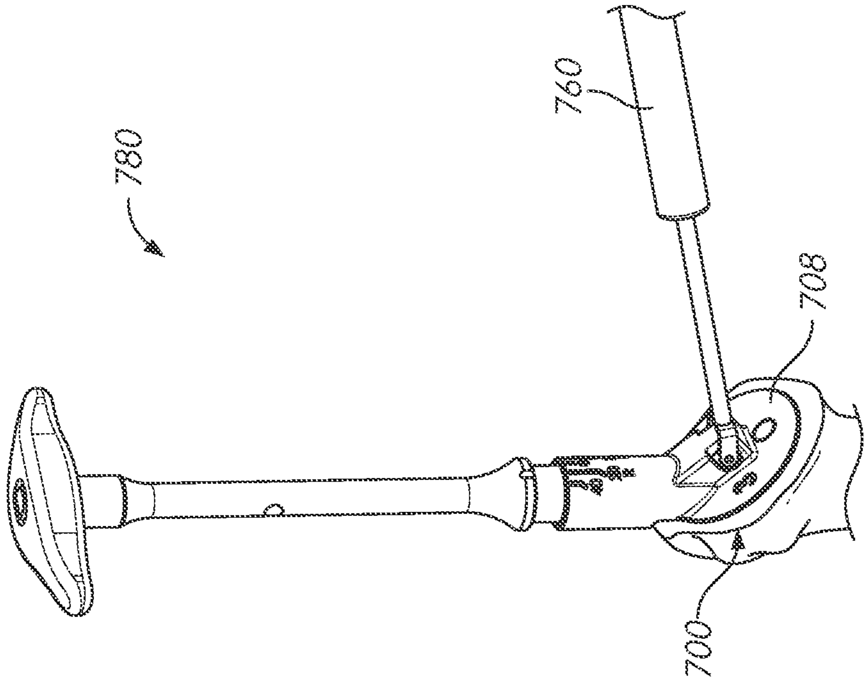
FIGS. 16A-16B illustrate steps for bone preparation using the humeral guide shown in FIG. 13A.

The surgeon may prefer to use a handle 760 to position the humeral guide 700 on the anatomy (see FIG. 16B). The humeral guide 700 can optionally include one or more handle attachment features 716, 718 configured to interface with a modular handle 760. The handle attachment features 716, 718 can extend from the second surface 708 in a central region thereof. For example, each handle attachment feature 716, 718 can be an opening extending in a transverse direction or perpendicular to a longitudinal axis L of the humeral guide 700 on a projection 717 extending from the second surface 708. Providing the handle attachment features 716, 718 in the central region of the humeral guide 700 prevents the guide from tilting when manipulating the handle.

The humeral guide 700 may form part of a kit including a plurality of humeral guides 700. The humeral guides 700 may vary in size as indicated by the size indicator 712. As explained above, the size of the humeral guide 700 may be selected based on a selected sizing disk that indicates the size of at least some of the tools and/or implants the surgeon should use to prepare the bone.

The kit may also include humeral guides 700 with different inclination angles between the guide feature 704 and the base 702. The inclination angle can be representative of a resection angle or a stem inclination angle, e.g., between an axis extending through a distal end of the stem and an axis extending through a proximal face of the stem of the final implant. The inclination angle can be measured between an axis aligned with a central longitudinal axis of an elongate distal portion of a stem and an axis extending perpendicular to a proximal face of the stem of the final implant. The inclination angle can be measured between an axis aligned with a central longitudinal axis of the humerus and an axis extending perpendicular to a proximal face of a humeral anchor with or without a stem portion. The inclination angle can provide the angle between a metaphyseal bowl portion and a stem portion of an implant. As shown, the humeral guide 700 has an inclination angle of 145 degrees, but the humeral guide 700 may have other inclination angles, for example angles of or between 125 degrees and 155 degrees, e.g., 135 degrees.

Figure 14:
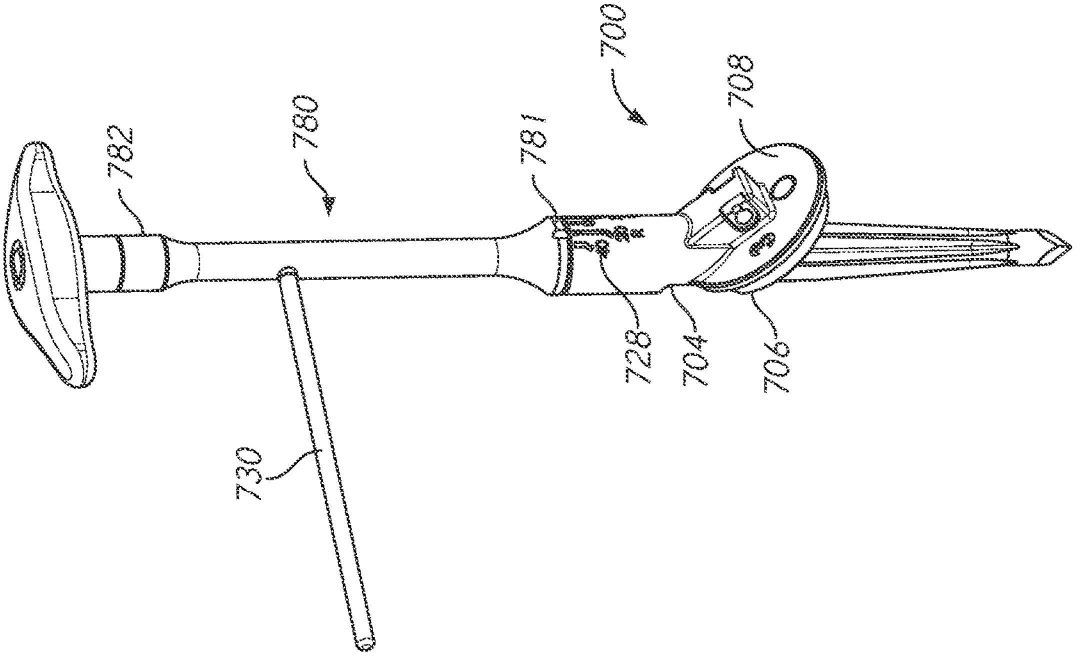
FIG. 14 illustrates the humeral guide shown in FIG. 13A with an awl extending through the guide feature.

FIG. 14 shows the humeral guide 700 with an awl 780 extending through the guide feature 704. The awl 780 may correspond to the selected size of the humeral guide 700. As shown in FIG. 14, the awl 780 may include a size indicator 782, for example a size specifying text, color, surface modifications, or combination of two or more such indicators. A single awl 780 may be suitable for more than one sized humeral guide 700.

Figure 15A:
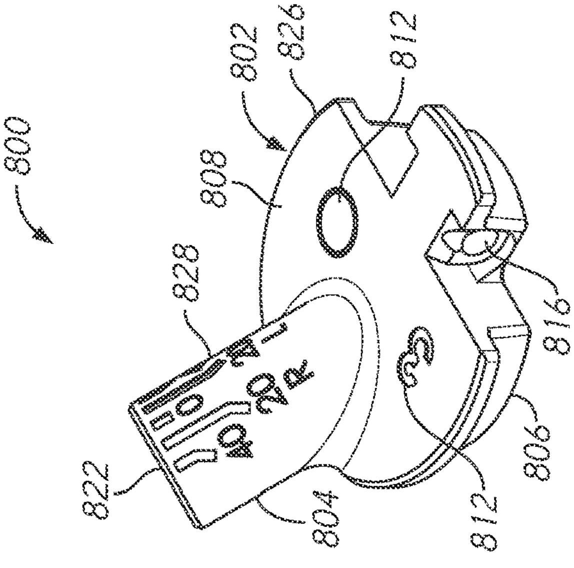
FIGS. 15A-15C illustrate another humeral guide.
Figure 15B:
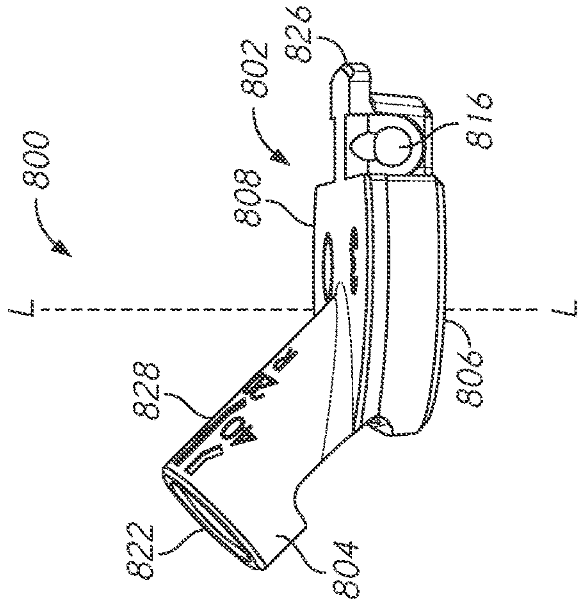
Figure 15C:
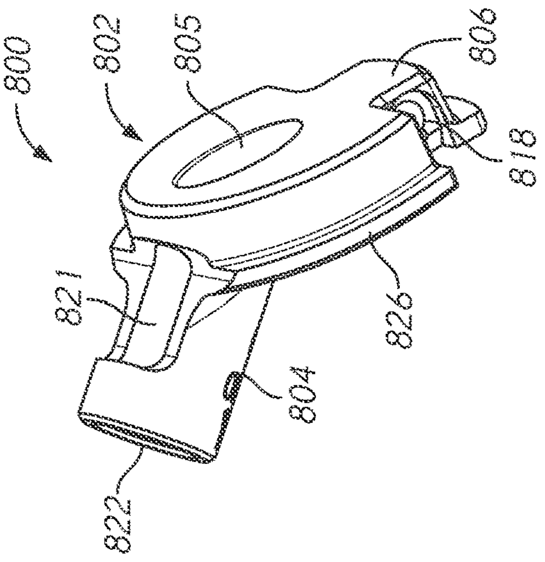

FIGS. 15A-15C show another humeral guide 800 that resembles the humeral guide 700 except as described below. Accordingly, numerals used to identify features of the humeral guide 700 are incremented by a factor of one hundred (100) to identify like features of the humeral guide 800. The description of the guide 700 will be considered to supplement the description of the guide 800 where consistent rather than repeating such descriptions. Similarly the descriptions of the guide 800 may supplement those of the guide 700.

As described above, the surgeon may prefer to use a handle to position the humeral guide on the anatomy. Accordingly, as shown in the FIGS. 15A-15C, the humeral guide 800 can optionally include one or more handle attachment features 816, 818 configured to interface with a modular handle (e.g., the handle 760 in FIG. 16B). The handle attachment features 816, 818 can be positioned at an inferior region of the humeral guide 800. For example, each handle attachment feature 816, 818 can be an opening extending in a transverse direction or perpendicular to a longitudinal axis L of the humeral guide 800. The handle attachment features 816, 818 can be disposed on a portion of the base 802 opposite to the guide feature 804. The handle attachment features 816, 818 can be located inferior of (or distal of) a second surface 808 of the guide 800. Providing the handle attachment features 816, 818 at the periphery of the base 802 makes it easier to machine the handle attachment features 816, 818.

As described above, a rear side of the humeral guide may include an open channel from the guide feature lumen to the first opening on the first surface of the humeral guide. However, other configurations are possible. For example, as shown in FIG. 15C, a rear side of the guide feature 804 may include a channel 821 providing access to the lumen of the guide feature 804. This channel 821 may be distinct from the first opening 805 on the first surface 806 of the humeral guide 800.

Figure 16A:
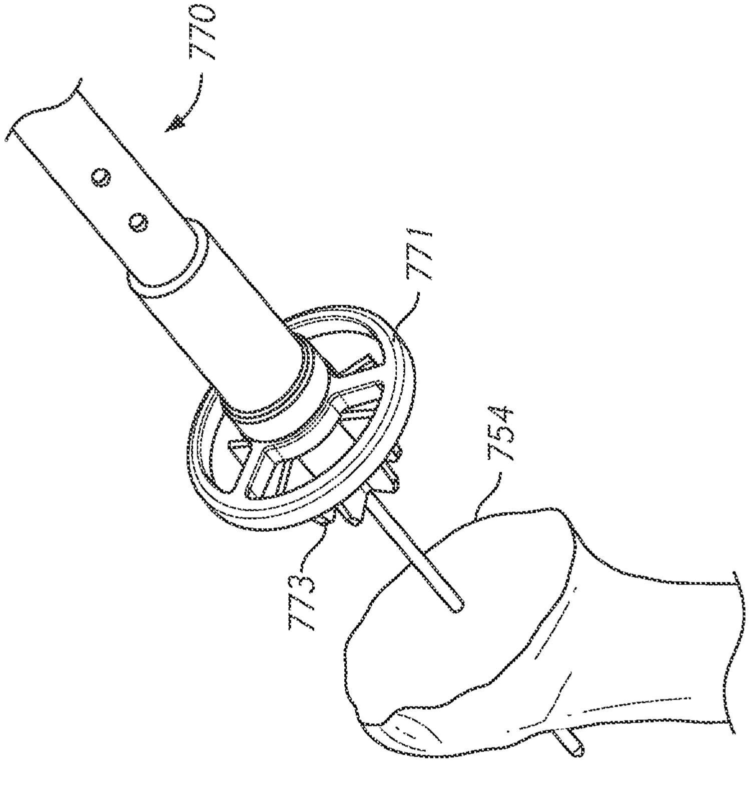

FIGS. 16A-16B illustrate a method of implanting a final implant using the humeral guide 700.

After the surgeon gains access to the humeral head, the superior or proximal end portion of the humerus is resected. The surgeon may evaluate the size of the metaphysis using any of the techniques described herein. For example, the surgeon may be provided with one or more sizing disks to determine a size of the metaphysis. Using the selected sizing disk, the surgeon can place a pin.

After selecting the appropriate sizing disk, a corresponding sized reamer 770 may be selected and delivered over the guide pin 754 to ream the metaphysis (see FIG. 16A). The guide pin 754 can be placed in the resected humerus using the selected sizing disk. The reamer 770 produces a cavity in the resected humerus. The cavity may be hemispherical, cylindrical, tiered, conical, or another shape such as including two or more cylindrical areas. For example, the reamer 770 may include a distal portion 773 configured to form a recess or surface in the metaphysis that generally matches the shape of the metaphyseal portion of a stemmed implant or all or a portion of an external surface of an anchor of a stemless implant, e.g., being an inverse thereof. The reamer 770 may also include a proximal portion 771 configured to form a recessed surface or counter sunk area below the resection plane. The recessed surface may surround at least a portion of the opening of the cavity. The recessed surface can be shaped to receive the depth stop 726 of the humeral guide 700 or the collar of a final implant. As shown in FIG. 16B, the humeral guide 700 is positioned in the bone such that the second surface 708 is flush with resection plane.

As shown in FIG. 16B, optionally, each humeral guide 700 can be positioned using a modular handle 760. The surgeon will select the appropriate humeral guide 700 based on the selected sizing disk. When positioned on the bone, the humeral guide 700 fits within the cortical boundary of the resected surface, but does not hang over the periphery of the resected surface.

Within each size, the surgeon may be provided with or may select one or more humeral guides 700 having different inclination angles, which can represent an angle relative to the face of the resection surface or the stem inclination angle of the final implant stem to be implanted. The inclination angle allows the surgeon to evaluate approximate stem axis position relative to the humeral canal before committing to the bowl placement in the metaphysis. The cylindrical extension of the guide feature 704 can provide a visual indicator of the inclination angle to help the surgeon select the appropriate inclination angle and/or verify that the angle of the resected surface is appropriate. If the cylindrical extension of the guide feature 704 is not in line with or parallel the diaphysis axis, then the angle of the resected surface may be off and the surgeon can recut the resected surface or make another adjustment to improve the positioning in the humerus.

After placing the appropriate humeral guide 700, the starter awl 780 or other tool is delivered through the guide feature 704 to create a pilot hole in line with the diaphysis axis. The pilot hole may extend toward or through the canal and in some techniques can extend at least the length of the final implant. Although not shown, after creating the pilot hole, different sized awls or sounders may be utilized to compact or otherwise prepare bone.

After reaming, a compactor may be selected based on the size and shape of the final implant. Compacting and following steps may include the same steps described above with respect to FIGS. 10E-10K.

Any of the guides described herein may have a patient specific design that matches the metaphyseal and diaphyseal axes of the patient's bone. The guides can be generated based on pre-operative or intra-operative imaging, such as CT scan, Mill scan, X-ray, or other imaging, and formed utilizing, for example, 3-D printing technology or the like.

Figure 17A:
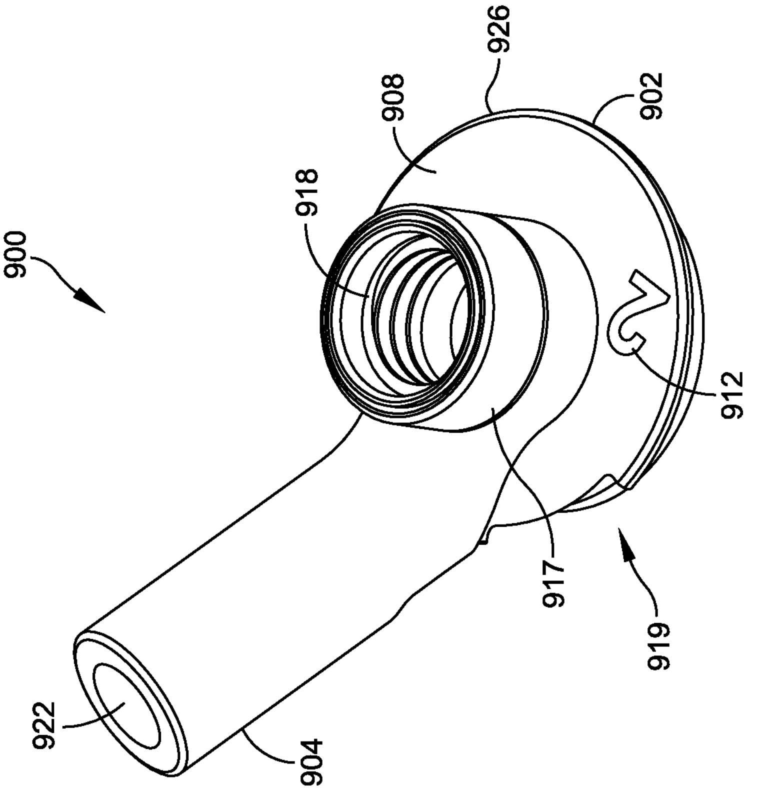
FIGS. 17A-17B illustrate humeral guide configured to guide an osteotome.
Figure 17B:
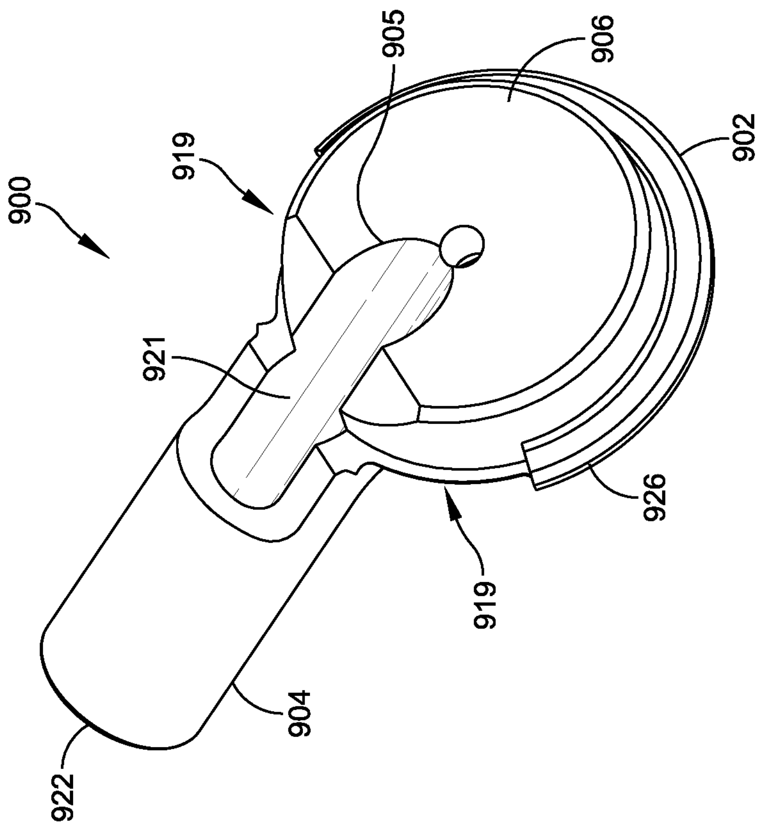

FIGS. 17A-17B illustrate another humeral guide 900. The humeral guide 900 can include any of the features of the above-described humeral guides.

As shown in FIGS. 17A-17B, the humeral guide 900 includes the base 902 and a guide feature 904. The base 902 includes a first or lateral surface 906 configured to contact a resected surface of a humerus, e.g., within the metaphysis, and a second or medial surface 908 opposite the first surface 906. As illustrated, the first surface 906 has a planar profile or configuration. However, the first surface 906 can take on any profile, including spherical, tiered, conical, cylindrical, or otherwise, for example depending on how the metaphysis is prepared.

The second surface 908 can include one or more indicators, for example text, color, surface modifications, etc., e.g., a size indicator of a particular size and/or inclination angle indicator of a particular angle of the humeral guide 900. As shown in FIG. 17A, the humeral guide 900 may include a size indicator 912, e.g., a text indicator conveying size information related to the guide 900 or an implant that can be placed following preparation involving the guide 900.

At least a portion of the second surface 908 may project radially outward of the first surface 906, thus forming the depth stop 926. The depth stop 926 may be configured to control a depth of insertion of the humeral guide 900 relative to the bone, e.g., relative to a resected or reamed surface. The shape and/or size of the depth stop 926 may correspond to the shape and/or size of a collar on the final implant. As explained above, the depth stop 926 rests on a recessed surface in the bone in some techniques.

As illustrated, the second surface 908 does not project radially outward of an entire circumference of the first surface 906. For example, the second surface 908 may only project radially outward of less than or equal to about 270 degrees, less than or equal to about 225 degrees, or less than or equal to about 180 degrees of a circumference of the first surface 906. The projecting portion of the second surface 908 can be located on an opposite side of the guide 900 compared to the location of the guide feature 904.

The guide feature 904 of the humeral guide 900 can be disposed on or accessible from the second surface 908. The guide feature 904 defines a lumen extending from a first opening 905 disposed on the first surface 906 of the base 902 to a second opening 922 disposed at an end of the guide feature 904 to such that a tool, e.g., an awl or sounder, can be advanced through the humeral guide 900. A rear side of the humeral guide 900 may include an open channel 921 forming a portion of the guide feature lumen extending to the first opening 905. The open channel 921 prevents the guide feature 904 from impinging on the resection. Although not required, the guide feature 904 can extend outwardly from (laterally of) a surface of the base 902 to provide additional stabilization and support for the tool. The guide feature 904 can have a cylindrical profile. In other configurations, the second opening 922 of the guide feature 904 may be positioned at or flush with the second surface 908.

The guide feature 904 is configured to guide a tool into a diaphysis of the bone along a central portion of a canal in the diaphysis. The guide feature 904 can be positioned at a superior side or region of the base 902 so the guide feature 904 can guide a tool into the diaphysis. The projecting portion of the second surface 908 can be located on an inferior side of the guide 900.

The surgeon may prefer to use a handle to position the humeral guide 900 on the anatomy. The humeral guide 900 can optionally include a handle attachment features 918 configured to interface with a handle. The handle attachment feature 918 can extend from a central region of the second surface 908. The handle attachment feature 918 may be a threaded attachment feature disposed within a projection 917 extending from the second surface 908. Fully enclosing the handle connection within the projection 917 prevents unintentional disengagement of the handle. Providing the handle attachment features 918 in the central region of the humeral guide 900 prevents the guide from tilting when manipulating the handle.

Figure 19B:
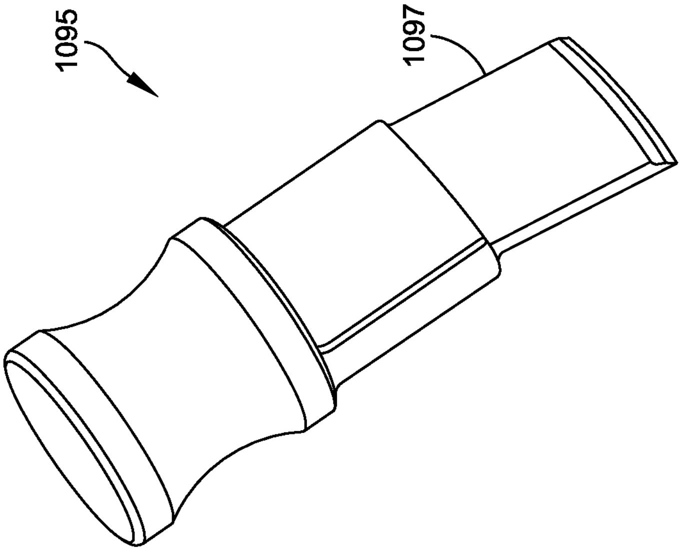
FIGS. 19A-19B illustrate an osteotome.
Figure 19A:
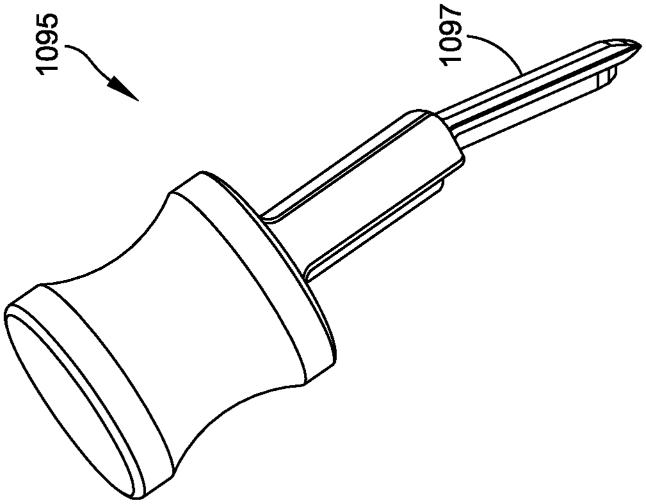

The base 902 can include one or more passageways 919 at a periphery of the base 902. The one or more passageways 919 provide access from the second surface 908 to the bone for a tool, such as an osteotome configured to remove additional bone. The one or more passageways 919 can be specifically shaped and/or sized to receive the blade of an osteotome, e.g., the osteotome 1095 of FIGS. 19A-19B. For example, each passageway 919 can have a similar profile to the blade 1097 of the osteotome 1095. Each passageway 919 can include an elongate shape with a length, measured in a circumference direction of the base 902, that is greater than a depth, measured in a radial direction of the base 902. When the osteotome 1095 is introduced into the passageway 919, the osteotome 1095 fills the entire passageway 919. Because the size of the passageway 919 corresponds to the size of the osteotome 1095, the osteotome 1095 does not have to be removed and reintroduced to remove additional bone underneath the slot. The osteotome 1095 can have a thickness corresponding to the radial direction of the base 902 that results in the blade 1097 extending radially outward of the circumference of the base 902. The passageway 919 can accommodate more than one osteotome 1095 where each of the more than one osteotomes has a different thickness corresponding to the radial direction of the base 902.

The one or more passageways 919 may extend along at least a portion of the periphery the base 902. As mentioned above, the second surface 908 project radially outward of only a partial circumference of the first surface 906. As shown in FIGS. 17A-17B, the passageways 919 may be disposed in the portion of the second surface 908 that does not project radially outward of the first surface 906. Together, the passageways 919 can extend less than or equal to 180 degrees, less than or equal to 135 degrees, or less than or equal to 90 degrees of the periphery of the base 902. Viewed another way, the one or more passageways 919 can take the form of a cutout in a periphery of the base 902. The one or more passageway 919 can be open or uncaptured cutouts in the base 902. Edges of the cutout may form a portion of the outer periphery of the base 902.

As shown in FIGS. 17A-17B, the guide 900 can include a pair of passageways 919. For example, the guide 900 can include a first passageway 919 on one side of the guide feature 904 and a second passageway 919 on the other side of the guide feature 904. Each passageway 919 can be disposed adjacent the guide feature 904, but in other embodiments, the passageways 919 can be spaced apart from the guide feature 904 and located anywhere along a periphery of the base 902.

Figure 18A:
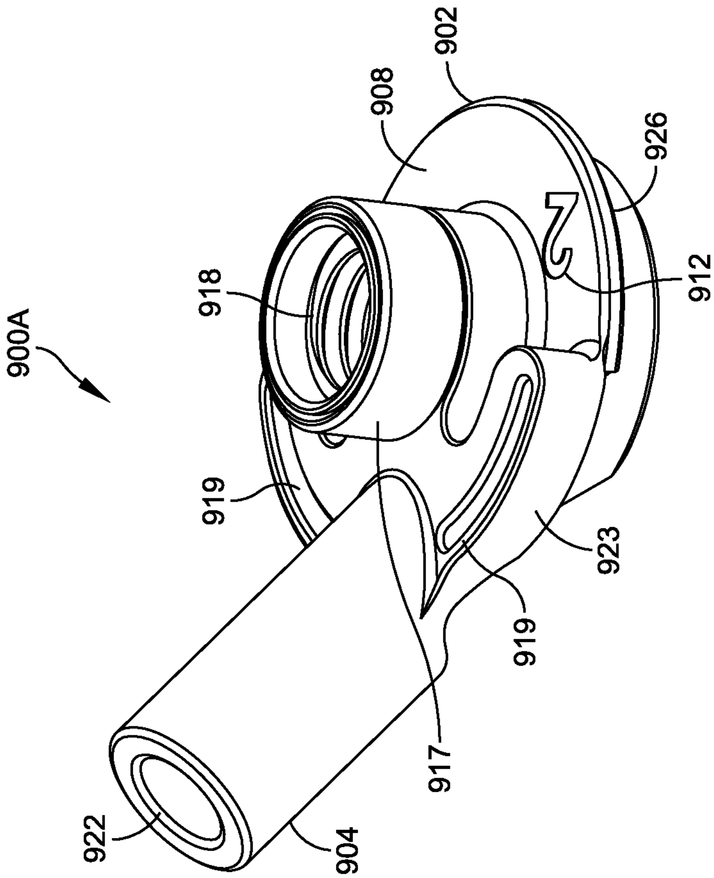
FIGS. 18A-18B illustrate another humeral guide configured to guide, e.g., to receive an osteotome.
Figure 18B:
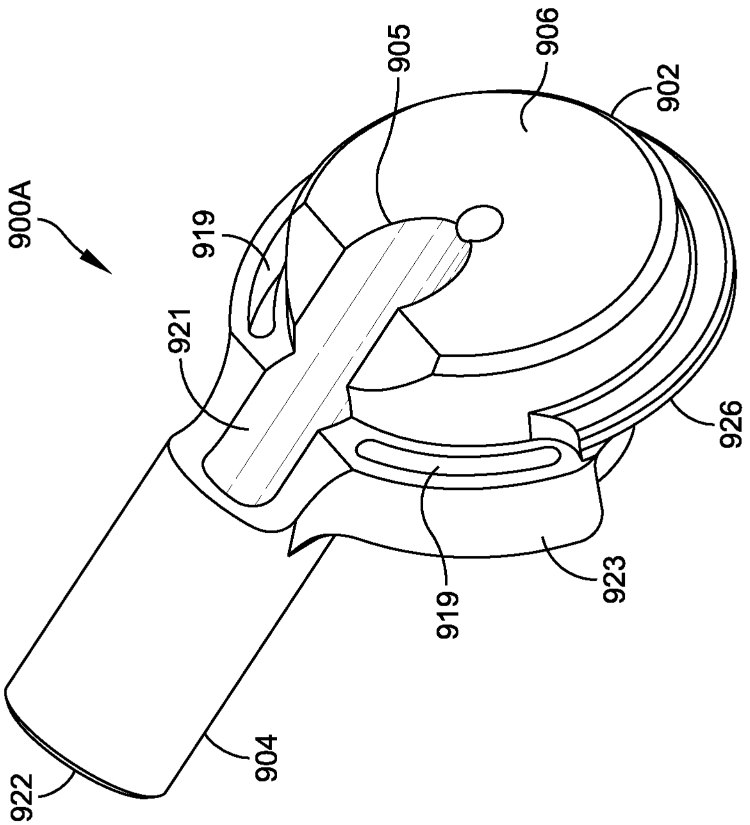

In other configurations, the one or more passageway 919 can be fully enclosed or captured passageways. For example, as shown in FIGS. 18A and 18B, the guide 900A can include a slot member 923 disposed along a periphery of the base 902. The one or more passageways 919 can be disposed in, e.g., be at least partially bounded by, the slot member 923 in the form of fully enclosed slots. At least a portion of the slot member 923 may extend from the second surface 908 and be disposed above the resection surface, in use, to provide support for the osteotome 1095. Once the osteotome 1095 is advanced through the captured passageway 919, the captured passageway 919 reduces, minimizes or prevents the osteotome 1095 from being inserted at the wrong angle or being angulated within the bone. In some configurations, the osteotome 1095 may form a clearance fit with the captured passageway 919 so the osteotome 1095 can be inserted into and removed from within the guide 900 while leaving the guide in place.

The slot member 923 can occupy or fill a space extended between two or more of the passageways 919, the guide feature 904, and the handle attachment 918. The slot member 923 can also extend medially, e.g., away from the second surface 908 in a direction opposite the first surface 906. As illustrated, the slot member 923 is integral with the base 902, but in other embodiments, the slot member 923 may be a separate component detachably attached to the base 902. Although FIGS. 18A-18B illustrate the slots formed in a slot member 923, the slots may be formed in the portion of the second surface 908 projecting radially beyond the first surface 906.

The humeral guide 900 may form part of a kit including a plurality of humeral guides 900. The humeral guides 900 may vary in size as indicated by the size indicator 912. As explained above, the size of the humeral guide 900 may be selected based on a selected sizing disk that indicates the size of at least some of the tools and/or implants the surgeon should use to prepare the bone. The kit may also include humeral guides 900 with different inclination angles between the guide feature 904 and the base 902.

The kit may include one or more osteotomes 1095 shaped and sized to be advanced through the passageways 919 in the humeral guides 900. For example, the kit may include a separate osteotome 1095 for each passageway 919. Each size of the humeral guide 900 may include the same sized passageways 919 or include different sized passageways 919 depending on the size of the guide 900. If the passageways 919 are different sizes, the kit may include different sized osteotomes 1095 that correspond to the different sized passageways 919.

FIGS. 20A-20K illustrate methods of implanting a final implant using the humeral guide 900A. After the surgeon gains access to the humeral head, the superior or proximal end portion of the humerus is resected.

Figures 20A, 20B, 20C, 20D, 20E, 20F, 20G, 20H:
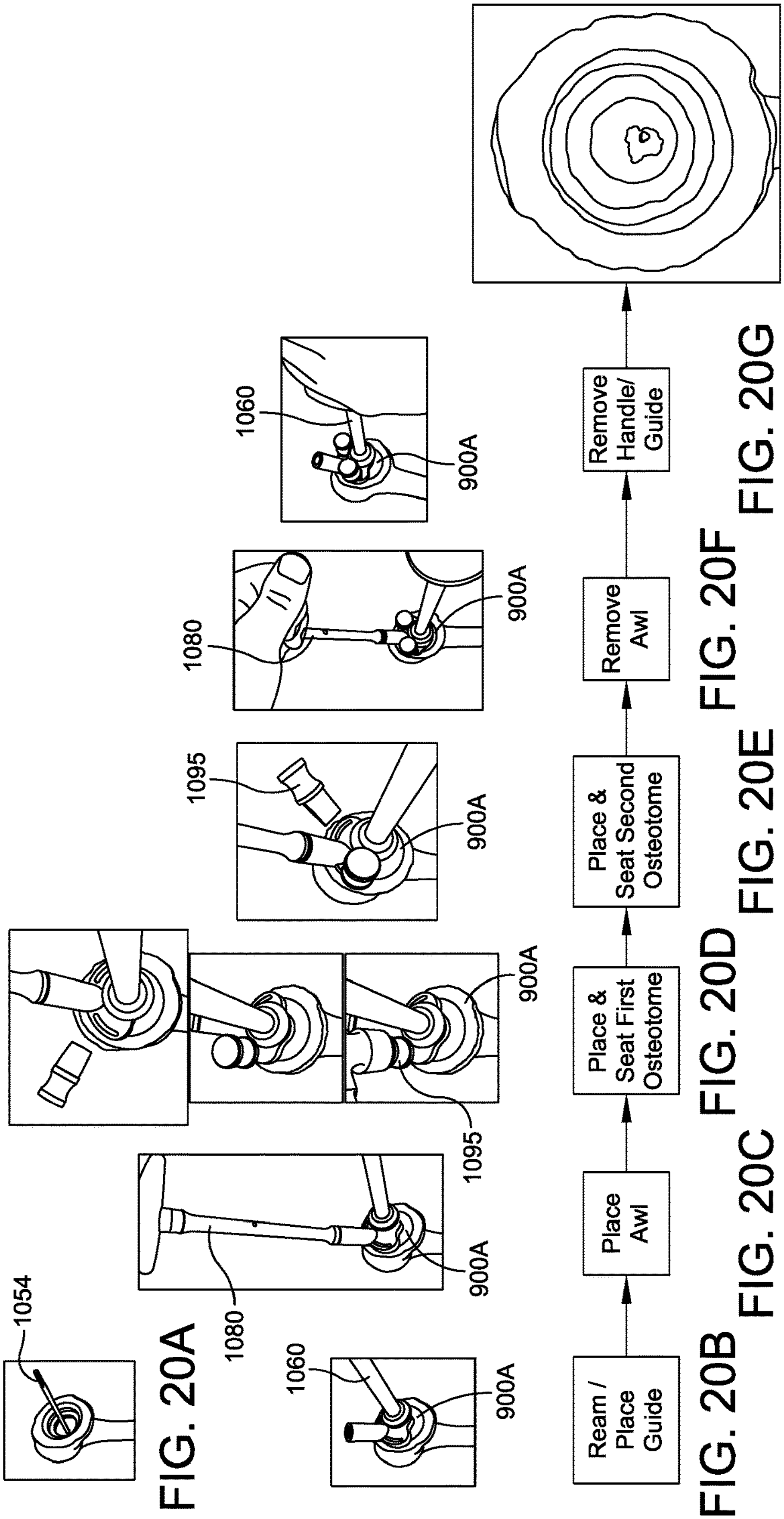
FIG. 20A-20H illustrate steps for bone preparation using the humeral guide shown in FIGS. 18A-18B.

As shown in FIG. 20A, the surgeon can place a central guide pin 1054. A reamer (not shown) may be selected and delivered over the central guide pin 1054 to ream the metaphysis. The reamer may produce a concavity in the resected surface of the bone, as shown in FIG. 20A. The concavity can generally match the shape of the metaphyseal portion of the final implant to be implanted.

After reaming, the first surface 906 of the humeral guide 900A may be positioned in the reamed cavity (see FIG. 20B). The humeral guide 900A may be positioned in the metaphysis using a handle 1060. The base 902 may be fully seated within the reamed cavity to provide metaphyseal referencing. As shown in FIG. 20C, a starter awl 1080 may be delivered through the guide feature 904 to create a pilot hole in line with the diaphysis axis. The pilot hole may extend toward or through the canal and in some techniques can extend at least the length of the final implant. Although not shown, after creating the pilot hole, different sized awls or sounders may be utilized to compact or otherwise prepare bone.

Prior to or following introduction of the awl 1080, a clinician may optionally decide to remove additional bone. For example, if the patient has dense bone material, the clinician may desire to remove additional bone. As shown in FIGS. 20D and 20E, the clinician may remove additional bone by introducing a first osteotome 1095 through a first passageway 919 in the guide 900 and introducing a second osteotome 1095 through a second passage 919 in the guide 900. However, if the patient has average or weak bone, the clinician may skip the steps shown in FIGS. 20D-20E to leave additional bone for stability.

After the bone has been prepared, the awl 1080 may be removed (see FIG. 20F). Thereafter, the handle 1060 and the guide 900 may be removed. The osteotomes 1095 may come out together with the guide 900. After the guide 900 has been removed, the bone includes a passageway along a central portion of a canal in the diaphysis (see FIG. 20H).

Figure 21B:
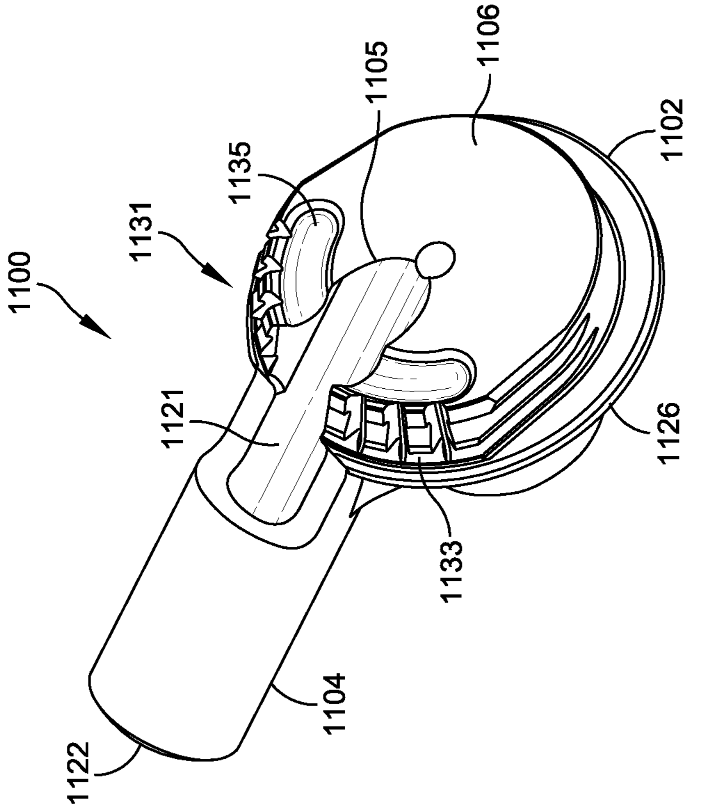
FIGS. 21A-21B illustrate a humeral guide with a cutting element.
Figure 21A:
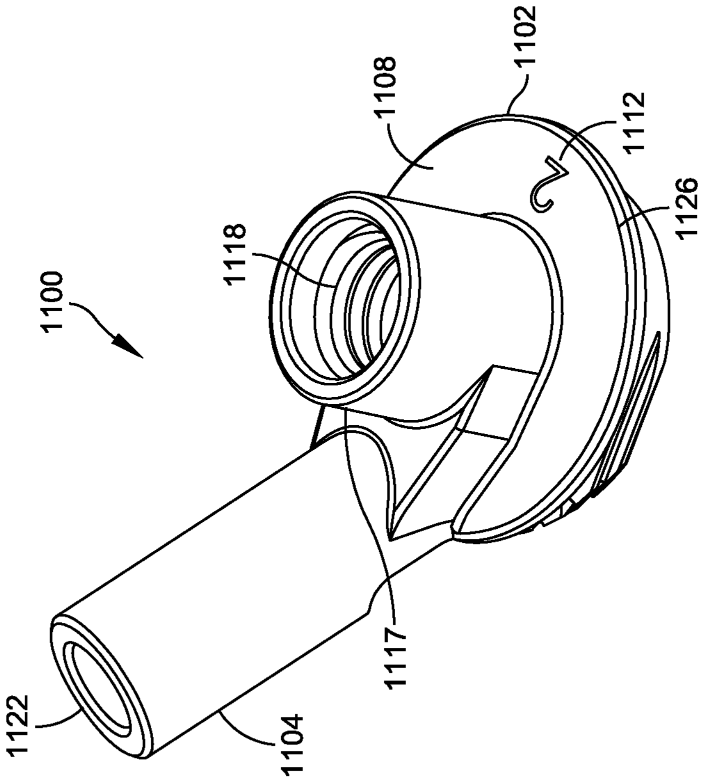

FIGS. 21A-21B illustrate another humeral guide 1100. The humeral guide 1100 can include any of the features of the above-described humeral guides.

As shown in FIGS. 21A-21B, the humeral guide 1100 includes the base 1102 and a guide feature 1104. The base 1102 includes a first or lateral surface 1106 configured to contact the metaphysis and a second or medial surface 1108 opposite the first surface 1106. As illustrated, the first surface 1106 has a planar profile or configuration. However, the first surface 1106 can take on any profile, including spherical, tiered, conical, cylindrical, or otherwise, for example depending on how the metaphysis is prepared.

The second surface 1108 can include one or more indicators, for example text, color, surface modifications, etc., e.g., a size indicator of a particular size and/or inclination angle indicator of a particular angle of the humeral guide 900. As shown in FIG. 21A, the humeral guide 900 may include a size indicator 1112, e.g., a text indicator.

The second surface 1108 may have a greater diameter than and project radially outward of the first surface 1106, thus forming the depth stop 1126. The depth stop 1126 may be configured to control a depth of the humeral guide 1100 relative to the bone. The shape and/or size of the depth stop 1126 may correspond to the shape and/or size of a collar on the final implant. As explained above, the depth stop 1126 rests on a recessed surface in the bone in some techniques.

The guide feature 1104 of the humeral guide 1100 can be disposed on or accessible from the second surface 1108. The guide feature 1104 defines a lumen extending from a second opening 1122 of the guide feature 1104 to a first opening 1105 of the base 1102 such that a tool can be advanced through the humeral guide 1100. A rear side of the humeral guide 1100 may include an open channel 1121 forming a portion of the guide feature lumen extending to the first opening 1105. The open channel 1121 prevents the guide feature 1104 from impinging on the resection. Although not required, the guide feature 1104 can extend outwardly from (laterally of) a surface of the base 1102 to provide additional stabilization and support for the tool. The guide feature 1104 can have a cylindrical profile. In other configurations, the second opening 1122 of the guide feature 1104 may be positioned at or flush with the second surface 1108.

The guide feature 1104 is configured to guide a tool into a diaphysis of the bone along a central portion of a canal in the diaphysis. The guide feature 1104 can be positioned at a superior side or region of the base 1102 so the guide feature 1104 can guide a tool into the diaphysis.

The surgeon may prefer to use a handle to position the humeral guide 1100 on the anatomy. The humeral guide 1100 can optionally include one or more handle attachment features 1118 configured to interface with a handle. The handle attachment feature 1118 can extend from a central region of the second surface 1108. The handle attachment feature 1118 may be a threaded attachment feature disposed within a projection 1117 extending from the second surface 1108. Fully enclosing the handle connection within the projection 1117 prevents unintentional disengagement of the handle. Providing the handle attachment features 1118 in the central region of the humeral guide 1100 prevents the guide from tilting when manipulating the handle.

The base 1102 can include a cutting feature 1131 for removing additional bone as the guide 1100 is advanced into the bone. For example, the cutting feature 1131 may punch out bone as the guide 1100 is advanced into the bone. Including the cutting feature 1131 on the guide 1100 may reduce the total number of tools needed to prepare the bone.

The cutting feature 1131 may be disposed along at least a portion of the periphery of the base 1102 or along the entire periphery of the base 1102. For example, as shown in FIG. 21B, the cutting feature 1131 may be disposed along at least a rear or superior portion of the base 1102. The cutting feature 1131 may be disposed on each side of the guide feature 1104. As shown in FIG. 21B, the cutting feature 1131 may include a plurality of rasp teeth 1133. Each tooth 1133 can generally extend in a longitudinal direction between the first surface 1106 and the second surface 1108 of the base 1102. The teeth 1133 may be positioned circumferentially around at least a portion of the periphery of the base 1102.

The humeral guide 1100 may also include a groove or channel 1135 disposed on the first surface 1106. The groove 1135 provides space for displaced bone fragments from the cutting feature 1131 cutting the bone. As shown in FIG. 21B, the groove 1135 may be adjacent to the cutting feature 1131. For example, the groove 1135 may be disposed along an edge of the cutting feature 1131, for example radially inward of the cutting feature 1131.

The humeral guide 1100 may form part of a kit including a plurality of humeral guides 1100. The humeral guides 1100 may vary in size as indicated by the size indicator 1112. As explained above, the size of the humeral guide 1100 may be selected based on a selected sizing disk that indicates the size of at least some of the tools and/or implants the surgeon should use to prepare the bone. The kit may also include humeral guides 1100 with different inclination angles between the guide feature 1104 and the base 1102.

Figure 22A:
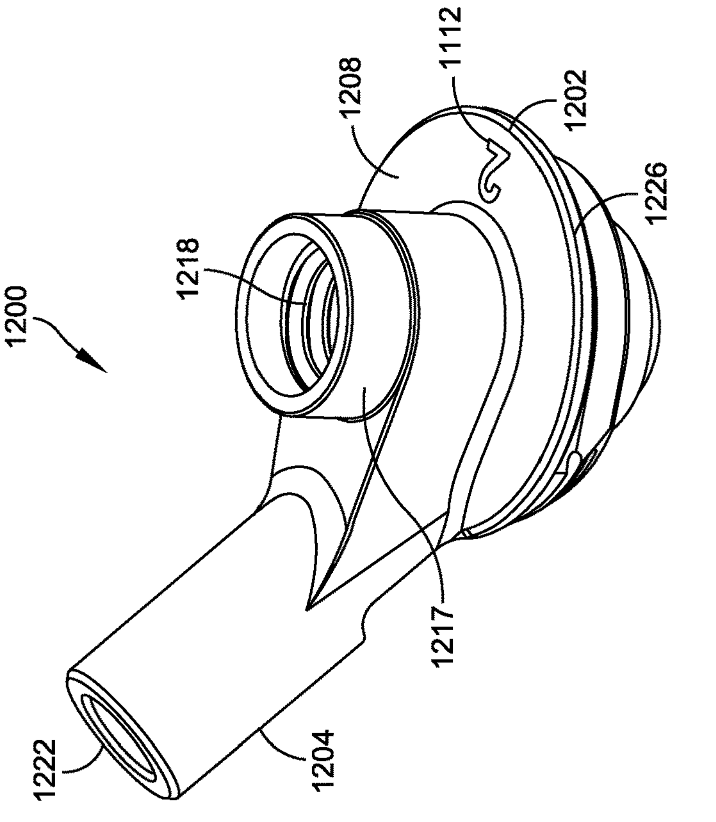
FIGS. 22A-22B illustrate another humeral guide with a cutting element.
Figure 22B:
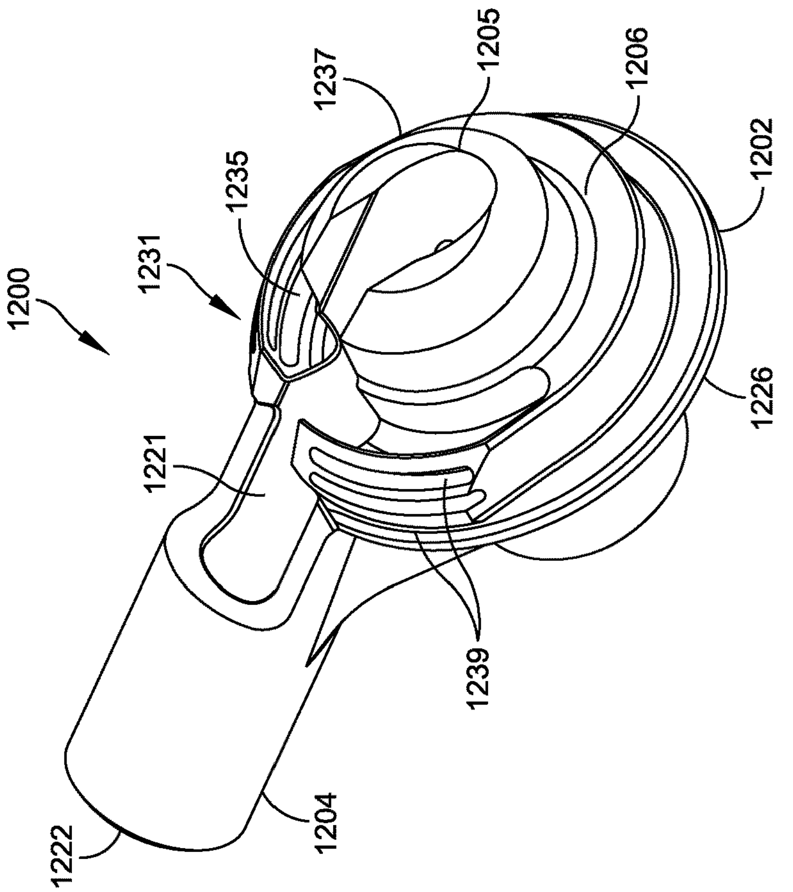

FIGS. 22A-22B illustrate another humeral guide 1200. The humeral guide 1200 is identical to the humeral guide 1100 except as described below.

The humeral guide 1200 includes the base 1202 and a guide feature 1204. The base 1202 includes a first or lateral surface 1206 configured to contact the metaphysis and a second or medial surface 1208 opposite the first surface 1206. As illustrated, the guide 1200 includes a pilot tip 1237 extending from the first surface 1206. The pilot tip 1237 can include a cylindrical, conical, frustoconical, or other shape. The pilot tip 1237 may facilitate introduction of the guide 1200 into the bone.

The guide feature 1204 of the humeral guide 1200 can be disposed on or accessible from the second surface 1208. The guide feature 1204 defines a lumen extending from a second opening 1222 of the guide feature 1204 to a first opening 1205 in the pilot tip 1237 such that a tool can be advanced through the humeral guide 1200. A rear side of the humeral guide 1200 may include an open channel 1221 from the guide feature lumen to the first opening 1205. The open channel 1221 prevents the guide feature 1204 from impinging on the resection. Although not required, the guide feature 1204 can extend outwardly from (laterally of) a surface of the base 1202 to provide additional stabilization and support for the tool. The guide feature 1204 can have a cylindrical profile. In other configurations, the second opening 1222 of the guide feature 1204 may be positioned at or flush with the second surface 1208.

The base 1202 can include a cutting feature 1231 for removing additional bone as the guide 1200 is advanced into the bone. For example, the cutting feature 1231 may punch out bone as the guide 1200 is advanced into the bone. Including the cutting feature 1231 on the guide 1200 may reduce the total number of tools needed to prepare the bone.

The cutting feature 1231 can be disposed along at least a portion of the periphery of the base 1202 or along the entire periphery of the base 1202. For example, as shown in FIG. 22B, the cutting feature 1231 may be disposed along at least a rear or superior portion of the base 1202. The cutting feature 1231 may be disposed on each side of the guide feature 1204. As shown in FIG. 22B, the cutting feature 1231 may include a plurality of blades 1239. Each blade 1239 can generally extend in a circumferential direction. The blades 1239 may be longitudinally displaced between the first surface 1206 and the second surface 1208. Some variations of the guide 1200 include arrays of blades 1239, e.g., two or more circumferential blades disposed along a radial direction of the guide 1200. The blades 1239 can a have a radial thickness transverse to their circumferential extent. The radial thickness of the blades 1239 can be more than radial spacing between adjacent blades. The radial thickness of the blades 1239 can be less than radial spacing between adjacent blades. The radial thickness of the blades 1239 can be about the same as the radial spacing between adjacent blades.

The humeral guide 1200 may also include a groove or channel 1235 disposed on the first surface 1206. The groove 1235 provides space for displaced bone fragments from the cutting feature 1231 cutting the bone. As shown in FIG. 22B, the groove 1235 may be adjacent to the cutting feature 1131. For example, the groove 1235 may be disposed between the cutting feature 1231 and the pilot tip 1237.

Terminology

As used herein, the relative terms "lateral" and "medial" shall be defined relative to the anatomy. Thus, medial refers to the direction toward the midline and lateral refers to the direction away from the midline.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 0.01 inches" includes "0.01 inches." Phrases preceded by a term such as "substantially" include the recited phrase and should be interpreted based on the circumstances (e.g., as much as reasonably possible under the circumstances). For example, "substantially linear" includes "linear."

What is claimed is:

1. A guide for guiding a tool into a medullary canal of a diaphysis of a bone having a resected surface, the guide comprising:

a base comprising a first portion having a first surface and a second portion having a second surface, the first surface sized and configured to be disposed in a metaphysis of the bone, and the second surface disposed on an opposite side of the base as the first surface;

a guide feature extending from at least a portion of the second surface of the second portion of the base in a direction non-orthogonal to the second surface and defining a lumen sized and configured to guide the tool along a central portion of the medullary canal of the diaphysis of the bone when the second portion of the base of the guide contacts the resected surface of the metaphysis of the bone; and a slot member extending from the second surface of the second portion of the base and in a direction proximally away from the first surface of the base, such that the slot member is disposed proximally above the first surface, the slot member defining one or more passageways disposed about a periphery of the base, each of the one or more passageways configured to receive an osteotome.

2. The guide of claim 1, wherein the one or more passageways comprises a pair of passageways.

3. The guide of claim 2, wherein each of the pair of passageways is disposed on either side of the guide feature.

4. The guide of claim 1, wherein the one or more passageways is one or more slots.

5. The guide of claim 4, wherein the slot member is disposed adjacent to the guide feature and the one or more slots have a depth to provide support for the osteotome.

6. The guide of claim 5, wherein the slot member is integral with the base.

7. The guide of claim 1, further comprising a handle attachment feature extending from a central region of the second surface.

8. The guide of claim 7, wherein the handle attachment feature is configured to threadably engage a handle.

9. The guide of claim 1, further comprising a pilot tip extending from the first surface of the base.

10. The guide of claim 9, wherein the lumen defined by the guide feature extends through the guide feature and the pilot tip.

11. The guide of claim 1, further comprising a cutting feature along at least a portion of a periphery of the base.

12. The guide of claim 11, further comprising a groove on the first surface of the base, the groove disposed adjacent to the cutting feature.

13. The guide of claim 1, wherein the guide feature extends from a superior region of the base.

14. The guide of claim 1, wherein the second portion defines a depth stop configured to contact the resected surface of the bone.

15. A guide for guiding a tool into a medullary canal of a bone, the guide comprising:

a base comprising:

a first surface configured to be disposed within a reamed metaphysis and contact a planar surface of the bone, and a second surface disposed on an opposite side of the base as the first surface, the second surface extending radially outwardly of the first surface such that the second surface is configured to function as a depth stop;

a guide feature extending from at least a portion of the second surface of the base in a direction away from the first surface of the base and defining a lumen sized and configured to guide a tool along a central portion of a medullary canal of the bone when the first surface is disposed within the reamed metaphysis, the guide feature comprising a sidewall and having a distal opening and a proximal opening; and a handle attachment feature extending from a central region of the second surface, the handle attachment feature comprising an interface configured to releasably engage a handle.

16. The guide of claim 15, wherein the guide feature is positioned at a superior region of the base.

17. The guide of claim 15, further comprising a pilot tip extending from the first surface of the base.

18. The guide of claim 17, wherein the lumen extends through the guide feature and the pilot tip.

19. The guide of claim 15, further comprising a cutting feature along at least a portion of a periphery of the base with a groove on the first surface of the base, the groove disposed adjacent to the cutting feature.

20. A guide for guiding a tool into a medullary canal of a diaphysis of a bone, the guide comprising:

a base comprising a first surface configured to contact the bone and a second surface opposite the first surface;

a guide feature disposed to guide a tool along a central portion of the medullary canal of the diaphysis of the bone; and a cutting feature for removing additional bone, the cutting feature including a plurality of rasp teeth arranged along at least a portion of a periphery of the base between the first portion of the base and the second portion of the base.

21. The guide of claim 20, wherein the cutting feature includes teeth disposed on either side of the guide feature.

22. The guide of claim 20, further comprising a groove on the first surface of the base, the groove disposed adjacent the cutting feature.

23. The guide of claim 20, further comprising a pilot tip extending from the first surface of the base.

24. The guide of claim 23, further comprising a lumen configured to receive the tool, the lumen extending through the guide feature and the pilot tip.

25. A method of preparing a-bone using the guide of claim 1, the method comprising:

positioning the first surface of the base of the guide onto the resected surface of the bone;

guiding the tool through the lumen defined by the guide feature of the guide and along the medullary canal of the diaphysis of the bone; and advancing the osteotome through at least one of the one or more passageways defined by the slot member and along the periphery of the guide.

26. The method of claim 25, wherein positioning the first surface of the guide onto the resected surface of the bone includes using a pilot tip on the guide.

27. The method of claim 25, further comprising threadably attaching a handle to a central region of the guide.

28. The method of claim 25, further comprising cutting the bone as the guide is advanced into the bone.

* * * * *